(12) United States Patent
Rhoads, Jr. et al.

(10) Patent No.: US 11,024,407 B2
(45) Date of Patent: Jun. 1, 2021

(54) DEVICE FOR OFFLOADING CAPPED VIALS USEFUL IN SYSTEM AND METHOD FOR DISPENSING PRESCRIPTIONS

(71) Applicant: Parata Systems, LLC, Durham, NC (US)

(72) Inventors: Thomas P. Rhoads, Jr., Raleigh, NC (US); Mark Longley, Raleigh, NC (US); Steve Bouchelle, Raleigh, NC (US); Bradley Kenneth Smith, Cary, NC (US); Eric X. Bonpain, Cary, NC (US); Robert Cenk Hernandez, Morrisville, NC (US); Matthew P. Daniels, Pittsboro, NC (US); Gary M. Owen, Wake Forest, NC (US)

(73) Assignee: Parata Systems, LLC, Durham, NC (US)

( * ) Notice: Subject to any disclaimer, the term of this patent is extended or adjusted under 35 U.S.C. 154(b) by 135 days.

(21) Appl. No.: 16/025,619

(22) Filed: Jul. 2, 2018

(65) Prior Publication Data
US 2019/0006035 A1    Jan. 3, 2019

Related U.S. Application Data

(63) Continuation of application No. 13/974,860, filed on Aug. 23, 2013, now abandoned.
(Continued)

(51) Int. Cl.
*G16H 20/10*    (2018.01)
*G07F 17/00*    (2006.01)
*G07F 11/16*    (2006.01)
*G07F 11/28*    (2006.01)
*G07F 11/30*    (2006.01)
*G16H 20/13*    (2018.01)

(52) U.S. Cl.
CPC ............. *G16H 20/13* (2018.01); *G07F 11/16* (2013.01); *G07F 11/28* (2013.01); *G07F 11/30* (2013.01); *G07F 17/0092* (2013.01); *G16H 20/10* (2018.01)

(58) Field of Classification Search
None
See application file for complete search history.

(56) References Cited

U.S. PATENT DOCUMENTS

| 5,208,762 A | * | 5/1993 | Charhut ................ A61J 7/0084 221/9 |
| 5,337,919 A | | 8/1994 | Spaulding et al. |
(Continued)

OTHER PUBLICATIONS

Bloss, Maybe the World's Largest Automated Assembly System, Assembly Automation, 2007, pp. 20-24, vol. 27, No. 1.
(Continued)

*Primary Examiner* — Nathaniel C Chukwurah
*Assistant Examiner* — Mobeen Ahmed
(74) *Attorney, Agent, or Firm* — Myers Bigel, P.A.

(57) ABSTRACT

An offloading unit for an automated pharmaceutical machine that dispenses filled, capped pharmaceutical vials includes at least one offload location; at least one tote to receive the vials at each offload location, the tote assigned for distribution to a remote pharmacy location; at least one sensor to detect the presence or absence of the tote; and at least one sensor to detect a fill level of the vials in the tote.

10 Claims, 18 Drawing Sheets

Related U.S. Application Data

(60) Provisional application No. 61/692,442, filed on Aug. 23, 2012, provisional application No. 61/813,431, filed on Apr. 18, 2013, provisional application No. 61/834,198, filed on Jun. 12, 2013.

(56) References Cited

U.S. PATENT DOCUMENTS

| | | | | |
|---|---|---|---|---|
| 5,419,457 | A * | 5/1995 | Ross | B07C 3/008 198/357 |
| 5,533,606 | A | 7/1996 | Yuyama | |
| 5,575,134 | A * | 11/1996 | Main | B65B 25/046 53/244 |
| 5,715,660 | A * | 2/1998 | Balentine | B65B 43/52 53/251 |
| 5,771,657 | A * | 6/1998 | Lasher | B65B 61/20 53/55 |
| 5,907,493 | A * | 5/1999 | Boyer | G06Q 10/087 700/231 |
| 6,006,946 | A | 12/1999 | Williams et al. | |
| 6,036,812 | A | 3/2000 | Williams et al. | |
| 6,176,392 | B1 | 1/2001 | William et al. | |
| 6,370,841 | B1 * | 4/2002 | Chudy | B65B 5/103 53/411 |
| 6,535,637 | B1 | 3/2003 | Wootton et al. | |
| 6,970,769 | B2 | 11/2005 | Rice et al. | |
| 6,971,541 | B2 | 12/2005 | Williams et al. | |
| 7,344,049 | B2 | 3/2008 | Daniels et al. | |
| 7,596,932 | B2 | 10/2009 | Sink et al. | |
| 7,748,199 | B2 * | 7/2010 | Sankaran | B65B 57/00 53/411 |
| 7,765,776 | B1 * | 8/2010 | Leu | B65C 9/1876 53/467 |
| 7,889,330 | B2 | 2/2011 | Newcomb | |
| 7,992,365 | B2 | 8/2011 | Uebel et al. | |
| 8,108,068 | B1 | 1/2012 | Boucher et al. | |
| 8,113,492 | B2 | 2/2012 | Cora et al. | |
| 8,195,328 | B2 * | 6/2012 | Mallett | A61B 90/96 700/236 |
| 8,196,774 | B1 * | 6/2012 | Clarke | G16H 40/67 221/197 |
| 8,224,482 | B2 * | 7/2012 | Schedel | G07F 11/62 700/240 |
| 8,244,398 | B2 | 8/2012 | Rivenbark, Jr. et al. | |
| 8,266,878 | B2 * | 9/2012 | Luciano, Jr. | G16H 20/13 53/473 |
| 8,284,305 | B2 | 10/2012 | Newcomb et al. | |
| 8,285,415 | B2 * | 10/2012 | Pandit | G06Q 10/08 700/230 |
| 8,345,989 | B1 | 1/2013 | Bresolin et al. | |
| 8,477,989 | B2 | 7/2013 | Bresolin | |
| 9,511,945 | B2 * | 12/2016 | Greyshock | B65G 35/00 |
| 10,053,248 | B2 * | 8/2018 | Joplin | B65B 35/56 |
| 10,315,450 | B1 * | 6/2019 | Luciano | G06Q 50/00 |
| 10,435,192 | B2 * | 10/2019 | Luciano, Jr. | B65B 25/00 |
| 2001/0017817 | A1 * | 8/2001 | De La Huerga | A61J 1/035 368/10 |
| 2002/0077771 | A1 * | 6/2002 | Mertens | B65B 1/48 702/156 |
| 2002/0103573 | A1 * | 8/2002 | Fellows | G07F 11/54 700/240 |
| 2004/0004085 | A1 | 1/2004 | Williams et al. | |
| 2004/0088187 | A1 * | 5/2004 | Chudy | G06Q 50/22 705/2 |
| 2004/0123567 | A1 * | 7/2004 | McErlean | G16H 20/13 53/445 |
| 2006/0010837 | A1 * | 1/2006 | Jurus | B65F 1/062 53/436 |
| 2008/0110555 | A1 * | 5/2008 | Bouchelle | B65C 9/32 156/230 |
| 2008/0110921 | A1 | 5/2008 | Dumond et al. | |
| 2008/0283179 | A1 | 11/2008 | Sink | |
| 2008/0283544 | A1 * | 11/2008 | Daniels | G07F 11/44 221/13 |
| 2009/0056285 | A1 * | 3/2009 | Kramer | G01N 35/04 53/492 |
| 2009/0173745 | A1 * | 7/2009 | Parrish | G07F 17/0092 221/2 |
| 2009/0173779 | A1 * | 7/2009 | Szesko | B65C 9/44 235/375 |
| 2009/0179041 | A1 | 7/2009 | Young et al. | |
| 2009/0287350 | A1 * | 11/2009 | Johnson | G16H 20/13 700/236 |
| 2009/0321465 | A1 * | 12/2009 | Knoth | G07F 17/0092 221/1 |
| 2010/0089997 | A1 * | 4/2010 | Carson | G07F 9/026 235/375 |
| 2010/0121999 | A1 * | 5/2010 | Isenmann | H04L 12/40006 710/105 |
| 2010/0138053 | A1 * | 6/2010 | Kollep | A47J 31/407 700/282 |
| 2010/0322822 | A1 * | 12/2010 | Fritchie | G01N 35/1065 422/63 |
| 2011/0160901 | A1 * | 6/2011 | Abrams, Jr. | G07F 17/0092 700/232 |
| 2011/0166878 | A1 * | 7/2011 | Louie | G06Q 50/22 705/2 |
| 2011/0313567 | A1 * | 12/2011 | Willemse | G07F 11/165 700/242 |
| 2012/0029692 | A1 * | 2/2012 | Owen | G01V 8/20 700/240 |
| 2012/0123907 | A1 * | 5/2012 | Luciano | G06Q 30/0641 705/27.1 |
| 2012/0152406 | A1 * | 6/2012 | Bartholomew | B65B 25/00 141/104 |
| 2012/0159907 | A1 * | 6/2012 | Henkel | B65B 5/103 53/500 |
| 2014/0123601 | A1 * | 5/2014 | Murokh | B41J 2/442 53/411 |
| 2014/0222181 | A1 * | 8/2014 | Hemenway | G06F 3/04817 700/97 |
| 2017/0269573 | A1 * | 9/2017 | Holzkamper | G05B 19/409 |

OTHER PUBLICATIONS

International Search Report and Written Opinion for corresponding PCT Application No. PCT/US2013/056325, dated Dec. 11, 2013.

* cited by examiner

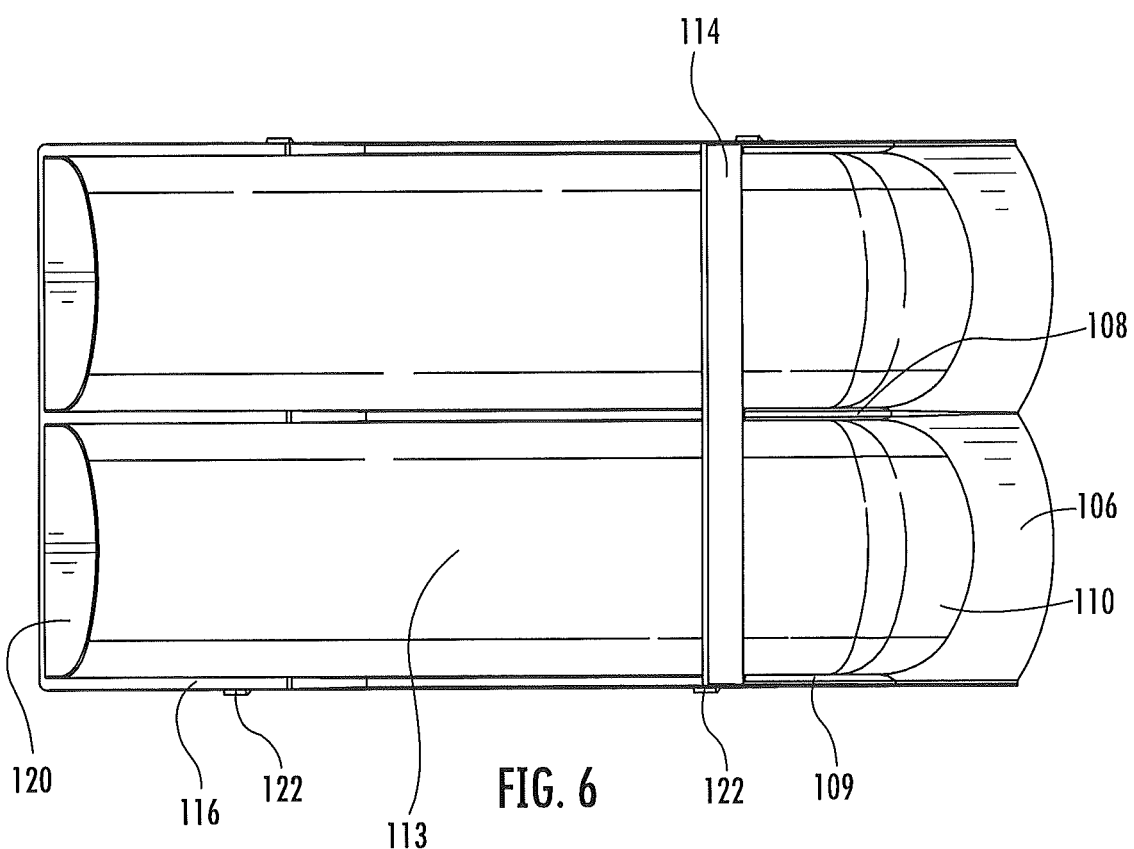

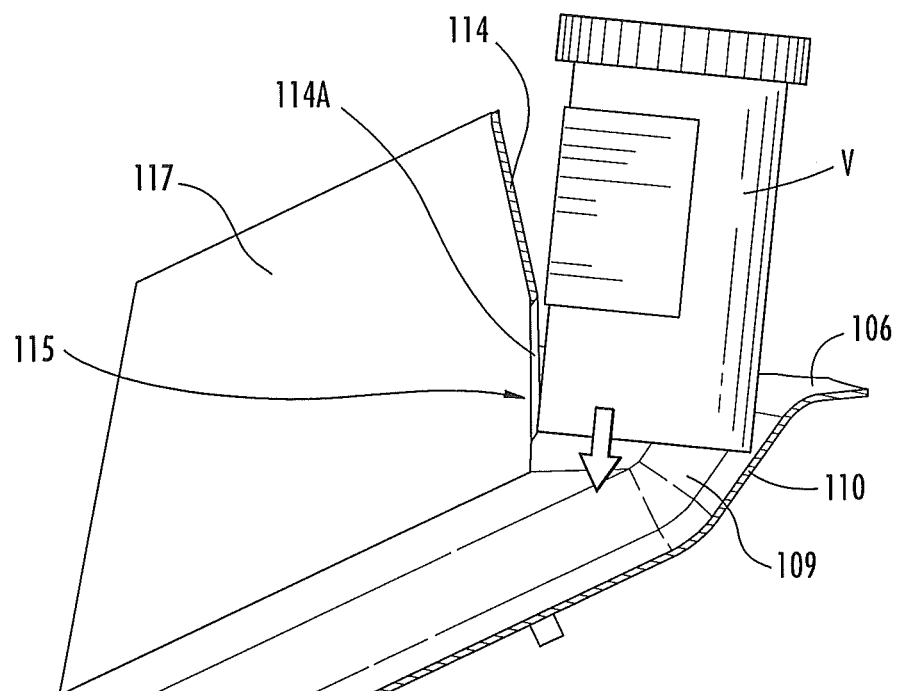
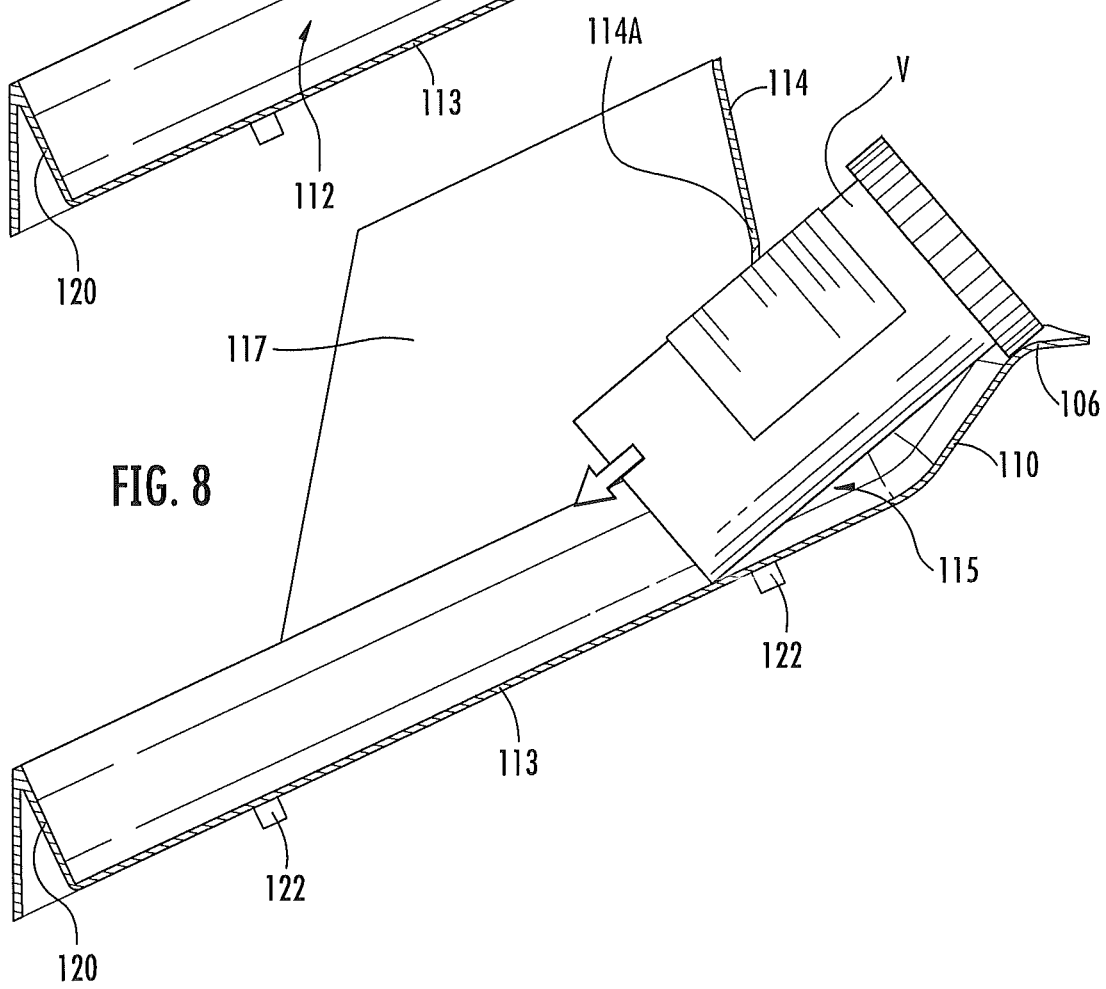

DEVICE FOR OFFLOADING CAPPED VIALS USEFUL IN SYSTEM AND METHOD FOR DISPENSING PRESCRIPTIONS

RELATED APPLICATIONS

The present application is a continuation application of and claims priority to U.S. patent application Ser. No. 13/974,860, filed Aug. 23, 2013, which claims the benefit of and priority from U.S. Provisional Patent Application No. 61/692,442, filed Aug. 23, 2012, U.S. Provisional Patent Application No. 61/813,431, filed Apr. 18, 2013, and U.S. Provisional Patent Application No. 61/834,198, filed Jun. 12, 2013, the disclosure of each of which is hereby incorporated herein in its entirety.

FIELD OF THE INVENTION

The present invention is directed generally to the dispensing of prescriptions of pharmaceuticals, and more specifically is directed to the automated dispensing of pharmaceuticals.

BACKGROUND OF THE INVENTION

Pharmacy generally began with the compounding of medicines which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable.

Some attempts have been made to automate the pharmacy environment. Different exemplary approaches are shown in U.S. Pat. No. 5,337,919 to Spaulding et al. and U.S. Pat. Nos. 6,006,946; 6,036,812 and 6,176,392 to Williams et al. The Williams system conveys a bin with tablets to a counter and a vial to the counter. The counter dispenses tablets to the vial. Once the tablets have been dispensed, the system returns the bin to its original location and conveys the vial to an output device. Tablets may be counted and dispensed with any number of counting devices. Drawbacks to these systems typically include the relatively low speed at which prescriptions are filled and the absence in these systems of securing a closure (i.e., a lid) on the container after it is filled.

One additional automated system for dispensing pharmaceuticals is described in some detail in U.S. Pat. No. 6,971,541 to Williams et al. This system has the capacity to select an appropriate vial, label the vial, fill the vial with a desired quantity of a selected pharmaceutical tablet, apply a cap to the filled vial, and convey the labeled, filled, capped vial to an offloading station for retrieval.

Although this particular system can provide automated pharmaceutical dispensing, certain of the operations may be improved. For example, the offload station of the system comprises a series of stationary holding compartments of conventional configuration. It may be desirable to provide an offload station having a different configuration that can improve speed and reliability of the system and allow for versatility of prescription filling options for the pharmacy.

SUMMARY OF THE INVENTION

As a first aspect, embodiments of the present invention are directed to an offloading unit for an automated pharmaceutical machine that dispenses filled, capped pharmaceutical vials, comprising: at least one offload location; at least one tote to receive the vials at each offload location, the tote assigned for distribution to a remote pharmacy location; at least one sensor to detect the presence or absence of the tote; and at least one sensor to detect a fill level of the vials in the tote.

As a second aspect, embodiments of the present invention are directed to a pharmaceutical dispensing system, comprising: a frame; a plurality of cells configured to house pharmaceutical pills; a processor; memory coupled to the processor; and a computer program residing in the memory that is executable by the processor for transmitting a message to one or more pre-identified locations about a status or function of the system.

As a third aspect, embodiments of the present invention are directed to a pharmaceutical dispensing system, comprising: a frame; a plurality of cells configured to house pharmaceutical pills; a processor; memory coupled to the processor; at least one offload location; at least one tote to receive the vials at each offload location, the tote assigned for distribution to a remote pharmacy location; at least one sensor to detect the presence or absence of the tote; at least one sensor to detect a fill level of the vials in the tote; and a GUI, wherein the GUI includes a portion specific to filling of the at least one tote.

BRIEF DESCRIPTION OF THE FIGURES

FIG. 6 is a top view of the chute unit of FIG. 4.

FIGS. 7-10 are sequence views of a vial traveling through the chute unit of FIG. 4, the chute unit being shown in side section view.

DETAILED DESCRIPTION OF EMBODIMENTS OF THE INVENTION

Figure 1:
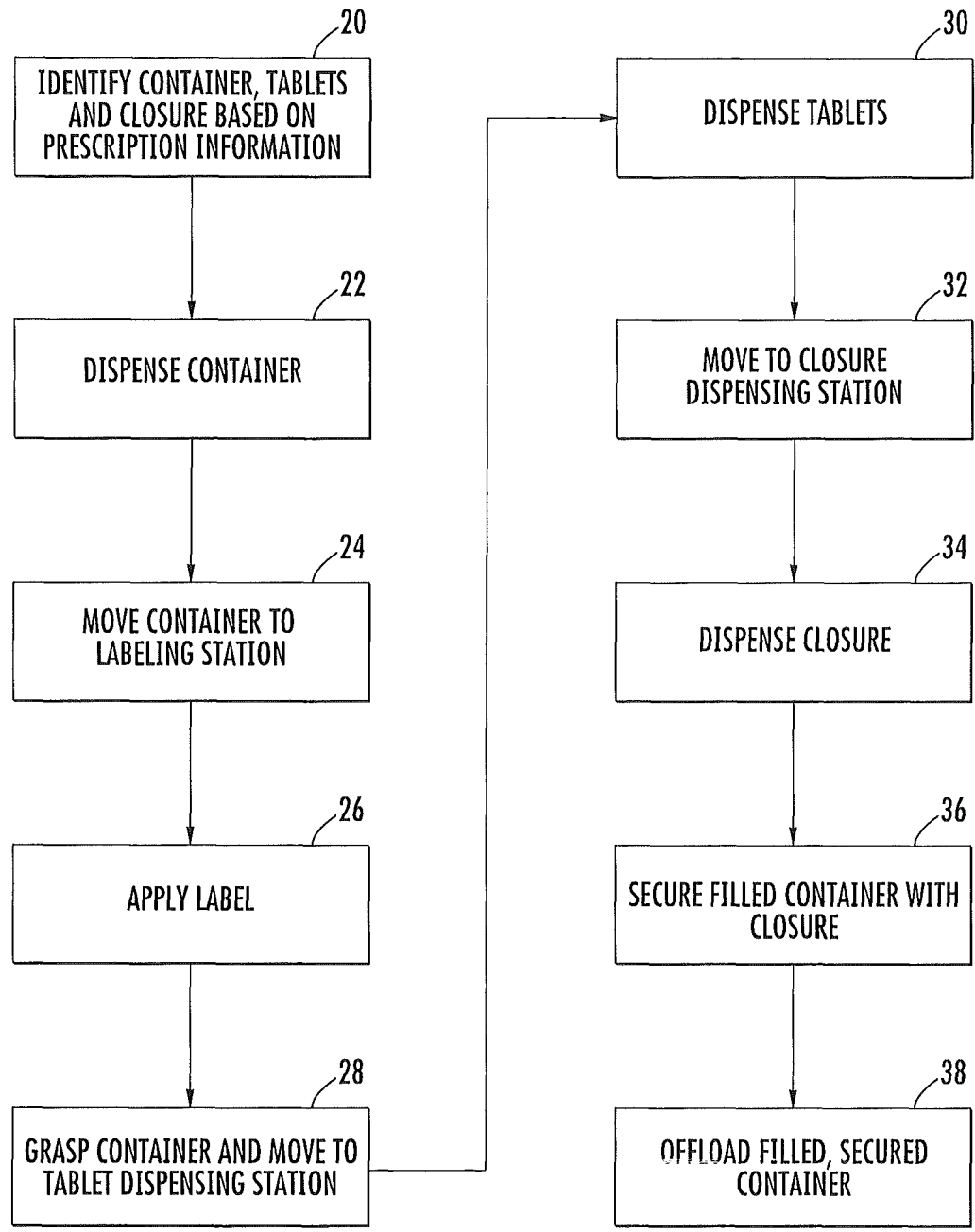
FIG. 1 is a flow chart of operations according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

As described above, the invention relates generally to a system and process for dispensing pharmaceuticals. An exemplary process is described generally with reference to FIG. 1. The process begins with the identification of the proper container, tablets or capsules and closure to be dispensed based on a patient's prescription information (Box 20). A container of the proper size is dispensed at a container dispensing station (Box 22), then grasped and moved to a labeling station (Box 24). The labeling station applies a label to the container (Box 26), after which the container is transferred to a tablet dispensing station (Box 28), from which the designated tablets are dispensed in the designated amount into the container (Box 30). The filled container is then moved to a closure dispensing station (Box 32), where a closure of the proper size has been dispensed (Box 34). The filled container is secured with a closure (Box 36), then transported to an offload station and offloaded (Box 38).

Figure 2:
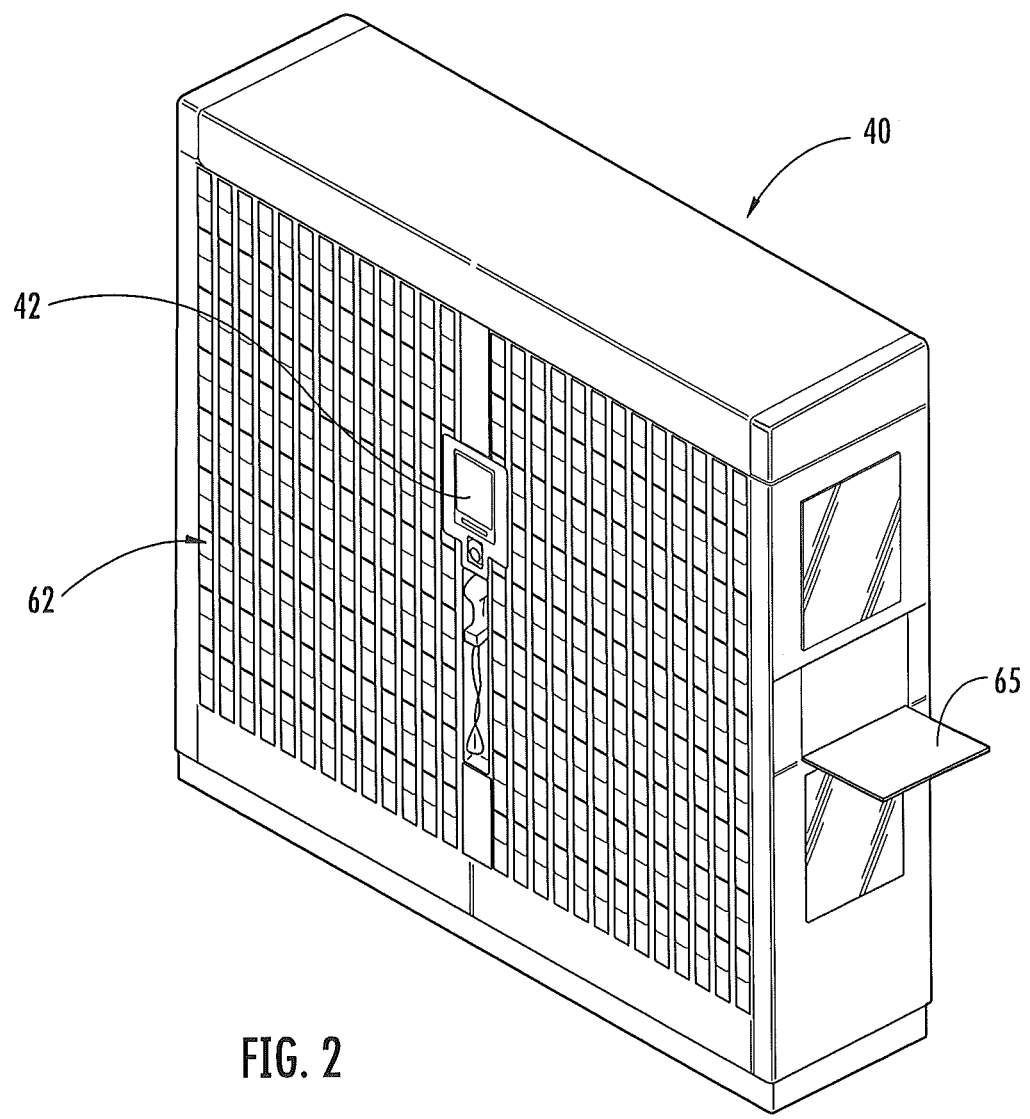
FIG. 2 is a top, front perspective view of a pharmaceutical dispensing system according to embodiments of the present invention.
Figure 3:
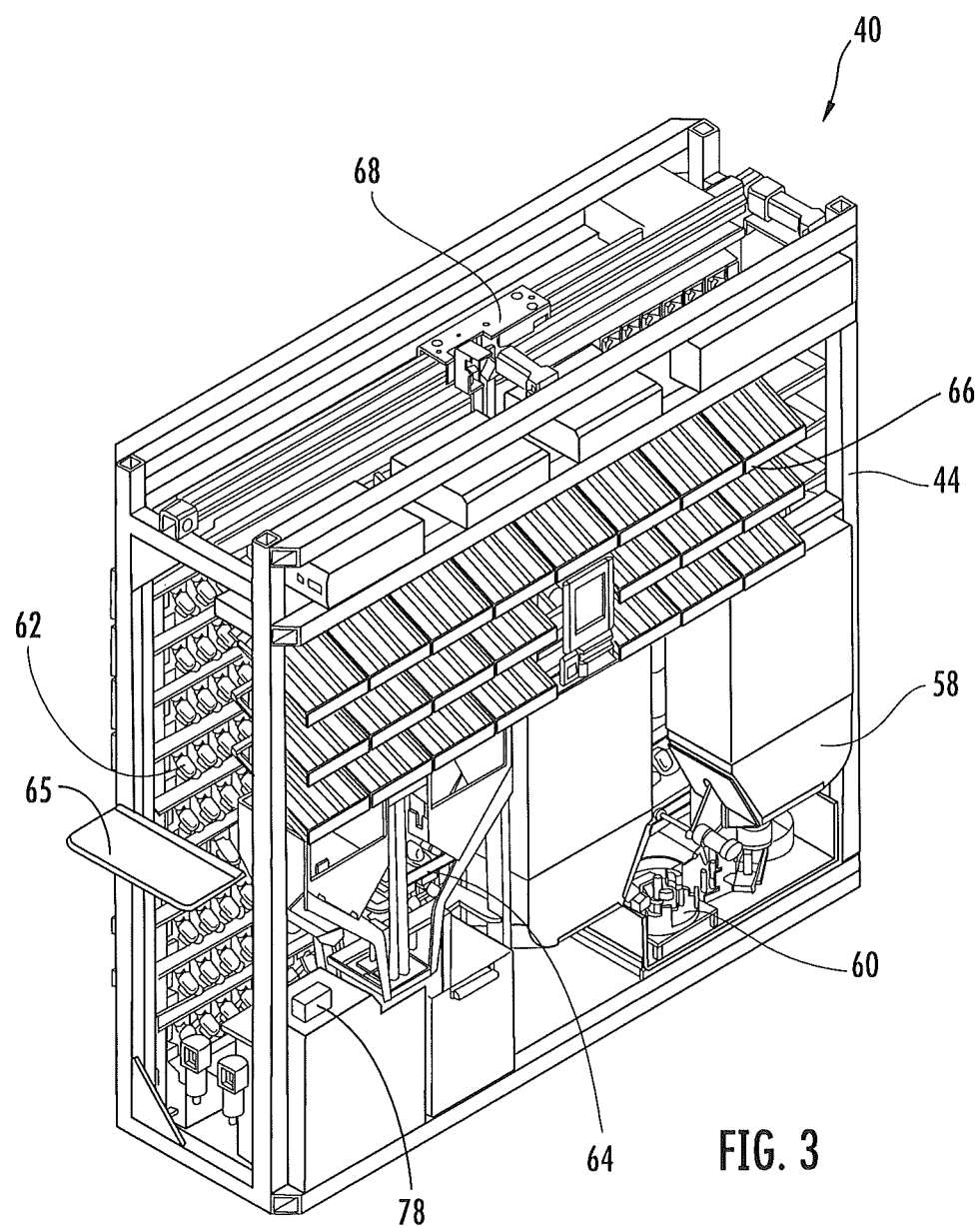
FIG. 3 is a top, rear perspective view of the system of FIG. 2 with the outer panel of the system removed to show the internal components.

A system that can carry out this process is illustrated in FIGS. 2 and 3 and designated broadly therein at 40. The system 40 includes a support frame 44 for the mounting of its various components. The system 40 generally includes as operative stations a controller (represented herein by a graphics user interface monitor 42), a container dispensing station 58, a labeling station 60, a tablet dispensing station 62, a closure station 64, and an offloading station 66. In the illustrated embodiment, containers, tablets and closures are moved between these stations with a single carrier 68; however, in some embodiments only a single carrier may be employed, or one or more additional carriers may be employed. The operation of the container dispensing station 58, the labeling station 60, the tablet dispensing station 62, and the closure station 64 are described in, for example, U.S. Patent Application Publication Nos. 2008/0110921 and 2008/0110555; and U.S. Pat. Nos. 7,596,932; and 7,344,049, the disclosures of each of which are hereby incorporated herein in its entirety. Additional components and features of the system are described in U.S. Patent Application Publication Nos. 2008/0283179 and 2009/0179041, and U.S. Pat. Nos. 8,113,492, 8,224,482, and 8,244,398, the disclosures of each of which are hereby incorporated herein in its entirety.

Figure 20:
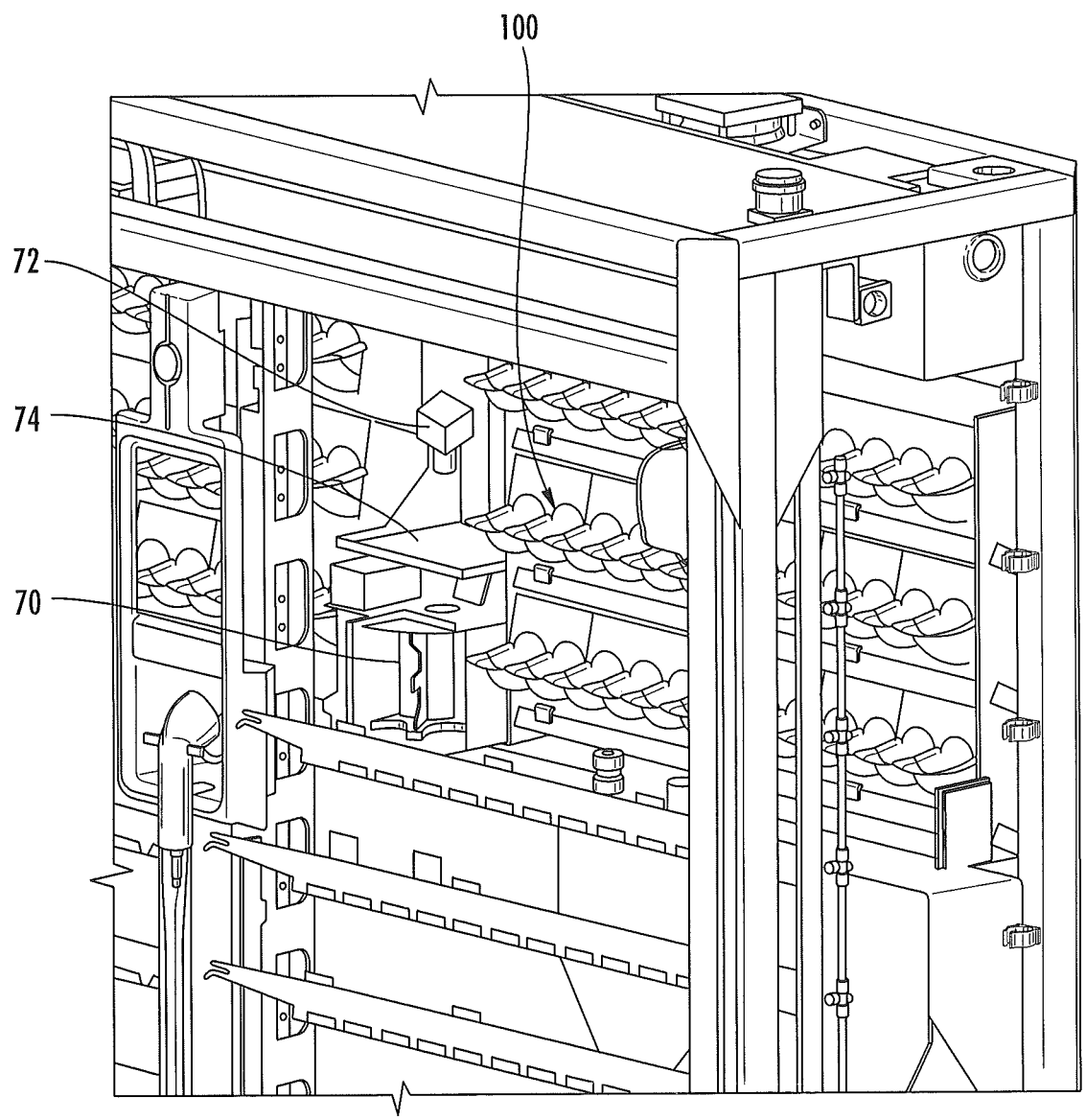
FIG. 20 is a partial perspective view of the system of FIG. 3 with some subsystems removed to show an exemplary imaging subsystem.

During the prescription filling process, a pharmacist typically must view the contents of the vial to verify that the prescription has been filled correctly. When the vial is filled in an automated system that includes a closure station 64, such as the system 40, the pharmacist must remove the cap on the vial to perform this verification. In some embodiments of the invention, the system 40 may include a camera 72 positioned such that it may capture an image of the contents of the vial prior to the vial being moved to the closure station 64 for capping. As shown in FIG. 20, the camera 72 may be located, for example, above an exception assembly 70 (for offloading of vials that encounter a problem in the filling process), but may be located in any other location where it will not interfere with other operations of the system 40. Once the pills have been dispensed into the vial, the carrier 68 may move the filled vial to a position, on a shelf 74, for example, near the camera 72 so that an image of the contents of the vial may be captured prior to capping the vial. In the illustrated embodiment, the camera 72 is situated so as to view and capture an image from the top of the vial. In some embodiments, the camera 72 and associated lighting system may be situated so as to capture the image of the pills through the vial, in which case the imaging step may occur before or after the capping step. Exemplary apparatus and methods for imaging the prescription through the vial can be found in U.S. Pat. Nos. 7,889,330; 8,284,305; 8,345,989; and 8,477,989, the disclosures of which are hereby incorporated by reference herein in their entirety. Images may be stored in the system 40 or at another location accessible to the system 40. The pharmacist may verify that the vial contains the correct drug by viewing the image of the contents of the vial. The pharmacist may view the image of the vial contents at a location that is proximate to the system 40 or in a remote location. Alternatively, automated image analysis may be employed to automatically verify the identity of the dispensed pharmaceutical and determine whether it matches the prescription that was requested. An exemplary image analysis system is described in U.S. Pat. No. 6,535,637, the disclosure of which is hereby incorporated by reference herein in its entirety. The system 40 may then report whether each prescription has passed the verification step; any vial that cannot be automatically verified may be flagged for manual verification by the pharmacist or for verification by some other process.

In another embodiment, a scale or other implementation of a weight sensor may be used in an additional verification process for the filling of the prescription. Exemplary systems employing a weight sensor to weigh the contents of a medication container are described in U.S. Pat. Nos. 8,108, 068 and 5,337,919, the disclosure of each of which is hereby incorporated by reference herein in its entirety. The scale may be otherwise incorporated into the system 40, including a stand-alone scale 78 (FIG. 3) on which the filled vial is deposited so that the weight may be determined. The scale 78 may be positioned in a location that is level and not subject to a significant amount of vibratory interference from other parts of the system 40. The scale 78 may be located on the shelf 74 (FIG. 20) upon which vials are placed for imaging; in this position, weighing and image capture can occur simultaneously, if desirable to do so. By comparing the total weight of the prescription vial and its contents with the expected weight of the filled prescription, the controller may provide another indication as to whether the prescription has been filled correctly. If the total weight of the vial and its contents does not match the expected weight of the filled prescription, the controller may direct steps to remedy the situation. For example, the controller may direct the carrier 68 to return the vial to the appropriate location in the tablet dispensing station 62 so that missing pills can be added, if the controller determines that the vial may be missing one or more pills because the weight of the vial and its contents is lower than expected. The controller may flag the vial with an error message indicating that the actual weight does not match the expected weight, so that pharmacy staff can investigate to determine if any errors had occurred in the filling process.

Turning now to FIG. 3, the offload station 66 includes a number of chute units 100, each of which, in the illustrated embodiment, includes two chutes 102, 104, although those skilled in this art will appreciate that a chute unit may include only a single chute or may include more than two chutes. Also, the offload station 66 may include only a single chute unit or any appropriate number of chute units.

Figure 4:
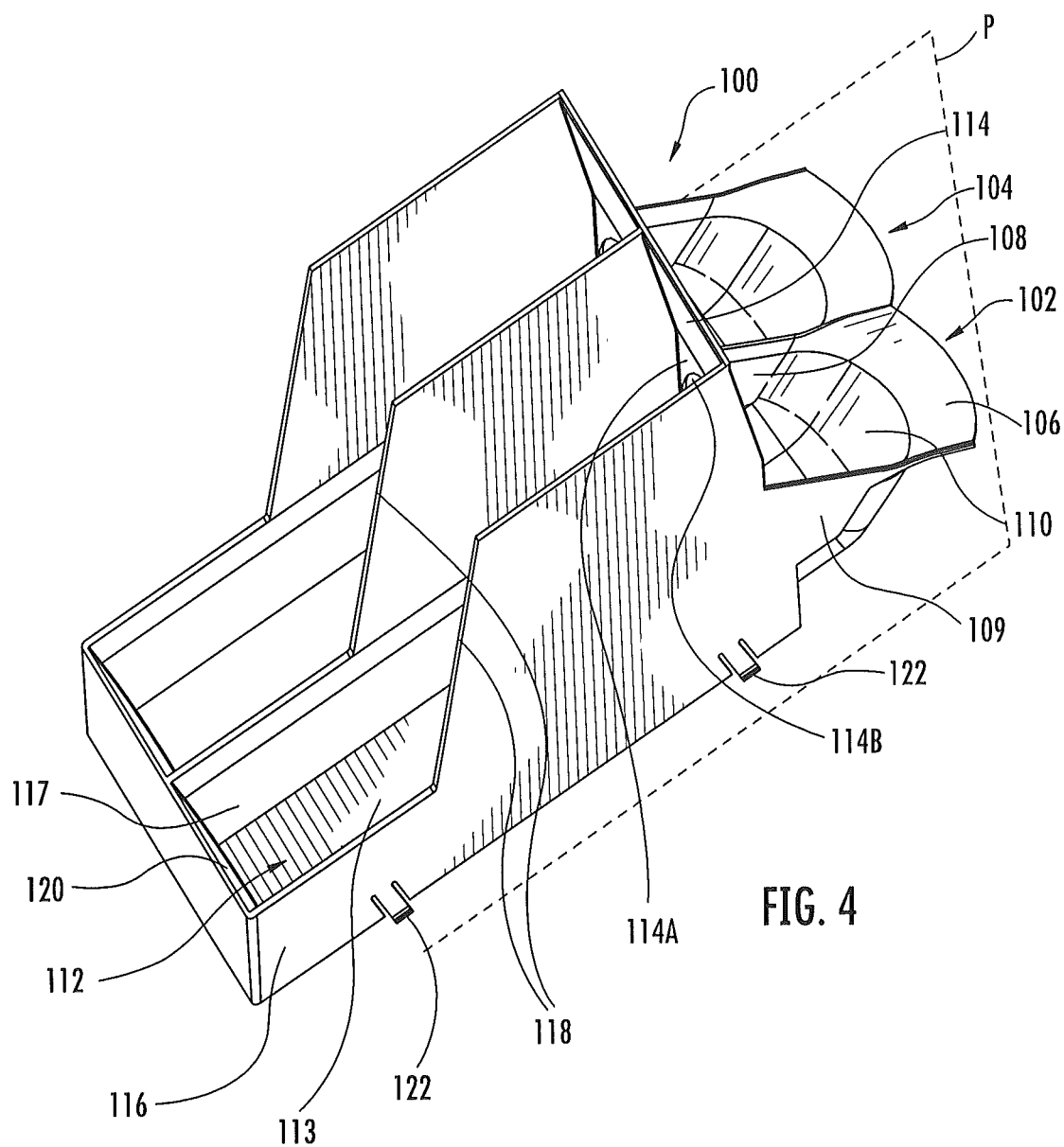
FIG. 4 is an isometric view of an offload chute unit according to the present invention.

The chutes 102, 104 are substantially identical mirror images of each other about a vertical plane P (see FIG. 4). As such, only the chute 102 will be described in detail herein, with the understanding that the description is equally applicable to the chute 104. For the purpose of this discussion, the terms "front," "forward" and derivatives thereof refer to the direction that a pharmaceutical vial travels in the chute 102, i.e., from right to left from the vantage point of FIG. 4. The terms "rear", "back" and derivatives thereof refer to the direction that is opposite of the "forward" direction, i.e., from left to right from the vantage point of FIG. 4. One may also think of the forward direction as extending "downstream" in the chutes 102, 104 and the rearward direction as extending "upstream" in the chutes 102, 104.

Figure 5:
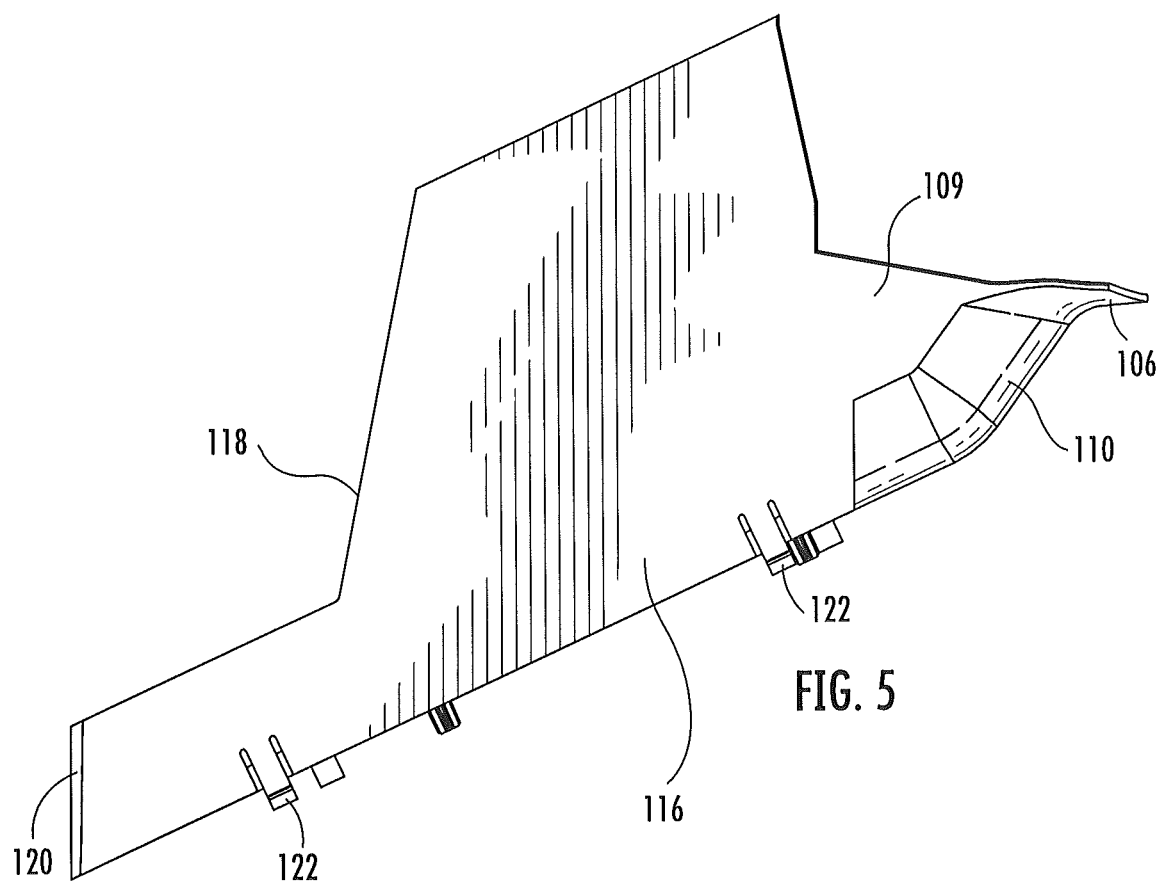
FIG. 5 is a side view of the chute unit of FIG. 4.
Figure 9:
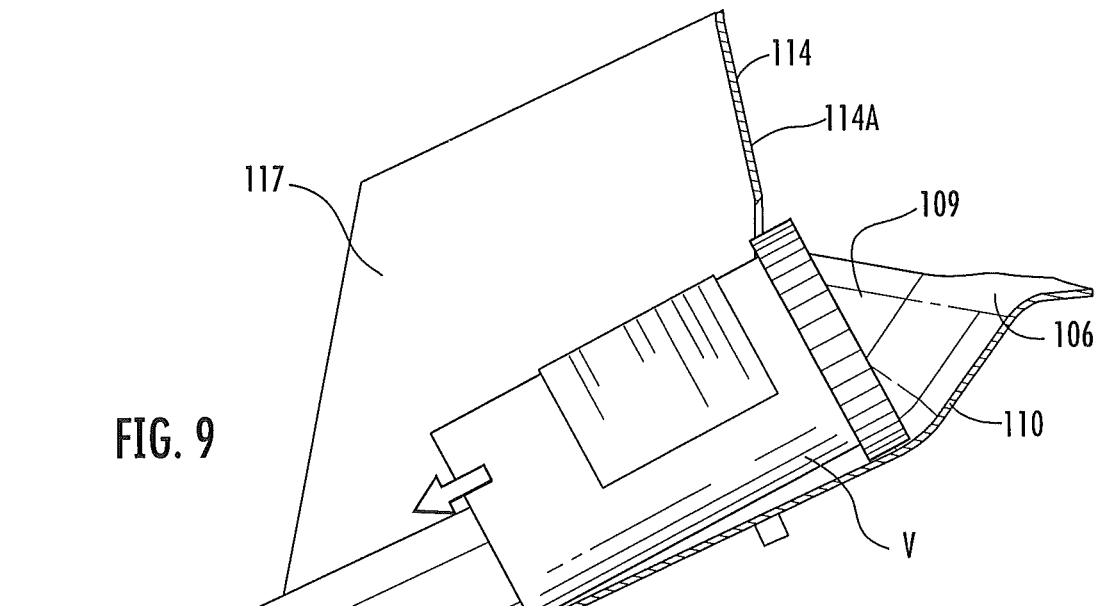
Figure 10:
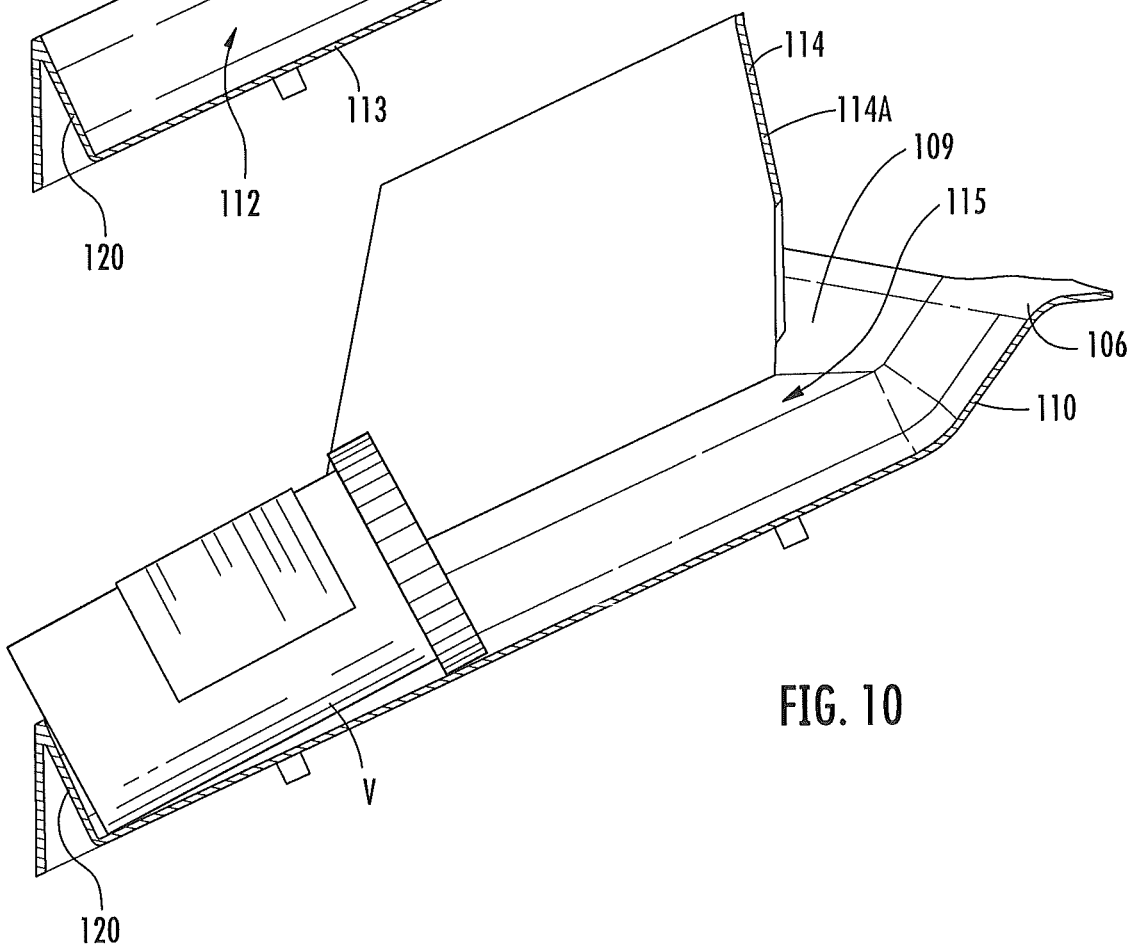

Referring again to FIG. 4 and also to FIGS. 5 and 6, the chute 102 has a rear lip 106 that resides above the frame 44. The lip 106 includes a shallow arc such that it is slightly concave. The lip 106 merges smoothly at its front end with a concave ramp 110. Side walls 108, 109 rise from the lateral edges of the ramp 110, with the forward ends of the side walls 108, 109 being higher than the rearward ends. The effect of the configuration provided by the lip 106, the ramp 110 and the side walls 108,109 is that of a half-bowl that drains downwardly into the remainder of the chute 102. The lower portion of the ramp 110 rests on the frame 44.

Still referring to FIGS. 4-6, a trough 112 having an arcuate profile extends forwardly and downwardly from the front end of the ramp 110. The trough 112 includes a concave floor 113 that is bounded at its lateral edges by dividers 116,117. A rear wall 114 rises above the rear end of the trough 112; the bottom portion 114*a* of the rear wall 114 angles rearwardly and has an arcuate lower edge 114*b* that, in combination with the rear end of the floor 113, forms an inlet 115 (see FIG. 7). At their rearward ends, the dividers 116, 117 are similar in height to the rear wall 114. Each of the dividers 116, 117 has a leading edge 118 that slopes sharply downward in a central portion of the divider 116, 117, such that the forward portion of the divider 116, 117 is relatively low. A front wall 120 spans the front ends of the troughs 112 and provides a landing area for vials. The front wall 120 may have a foam or other shock absorbent material attached thereto to reduce any rebound effect of the vial dropping down the chute 102 and striking the front wall 120.

The chute unit 100 is attached to the frame 44 via four latches 122. The latches 122 are inserted into mating apertures (not shown) in the frame 44. In the illustrated embodiment, the chute unit 100 is mounted so that the troughs 112 slope downwardly from back to front; for example, the chute unit 100 may be mounted such that the trough 112 is angled relative to a horizontal plane at an angle of between about 20 and 35 degrees.

In the illustrated embodiment, the chute unit 100 is formed as a unitary member, although those skilled in this art will appreciate that the chute unit may be formed with multiple components. The chute unit 100 may be formed of any material recognized as being suitable for the conveying of objects such as pharmaceutical vials; exemplary materials include polymeric materials such as polycarbonate, ABS and copolymers and blends thereof.

Referring now to FIGS. 7-10, in operation, after a vial V has been dispensed, labeled, filled and capped, it is transported by the carrier to the offload station 66. The carrier 70 deposits the vial V "right-side up" into the half-bowl formed by the lip 106, the side walls 108, 109, and the ramp 110 (see FIG. 7); the angled bottom portion 114*a* of the rear wall 114 can also assist in funneling the vial V into position. In some embodiments, the dimensions of the lip 106, ramp 110, side walls 108, 109 and bottom portion 114*a* of the rear wall 114 are selected to ensure that a "right side up" vial V presented by the carrier 70 exits the "half-bowl" with the lower (i.e., non-capped) end leading the upper, capped end, irrespective of which of multiple common vial sizes is presented (see FIG. 8). Typically, the length of a capped vial V is between about 2 and 4 inches, and the diameter is between about 1.25 and 2.0 inches. In some embodiments, the distance between the side walls 108, 109 is between about 2.5 and 2.75 inches, the ramp 110 has a depth of about 1.5 to 2.0 inches, the distance from the rear edge of the ramp 110 to the rear edge of the bottom portion 114*a* of the rear wall 114 is between about 3.25 and 3.5 inches, and the ramp 110 generally forms an angle of between about 20 and 30 degrees relative to an underlying horizontal surface.

Figure 13:
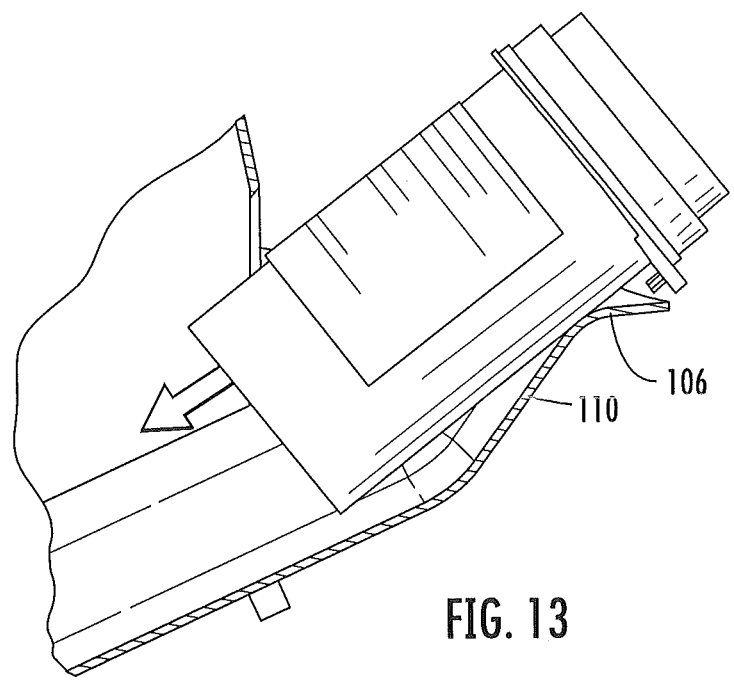
FIG. 13 is an enlarged side section view illustrating a reversible closure (RC) vial entering the chute unit of FIG. 4.

Also, the smoothly merging side walls 108, 109, lip 106 and ramp 110 are configured such that vials do not snag or hang thereon. In particular, vials known as "RC" vials (available from Owens-Corning, Owens, Ill.), have a finger on the edge thereof that might be susceptible to being caught on an unsmooth surface (see FIG. 13).

Figure 11:
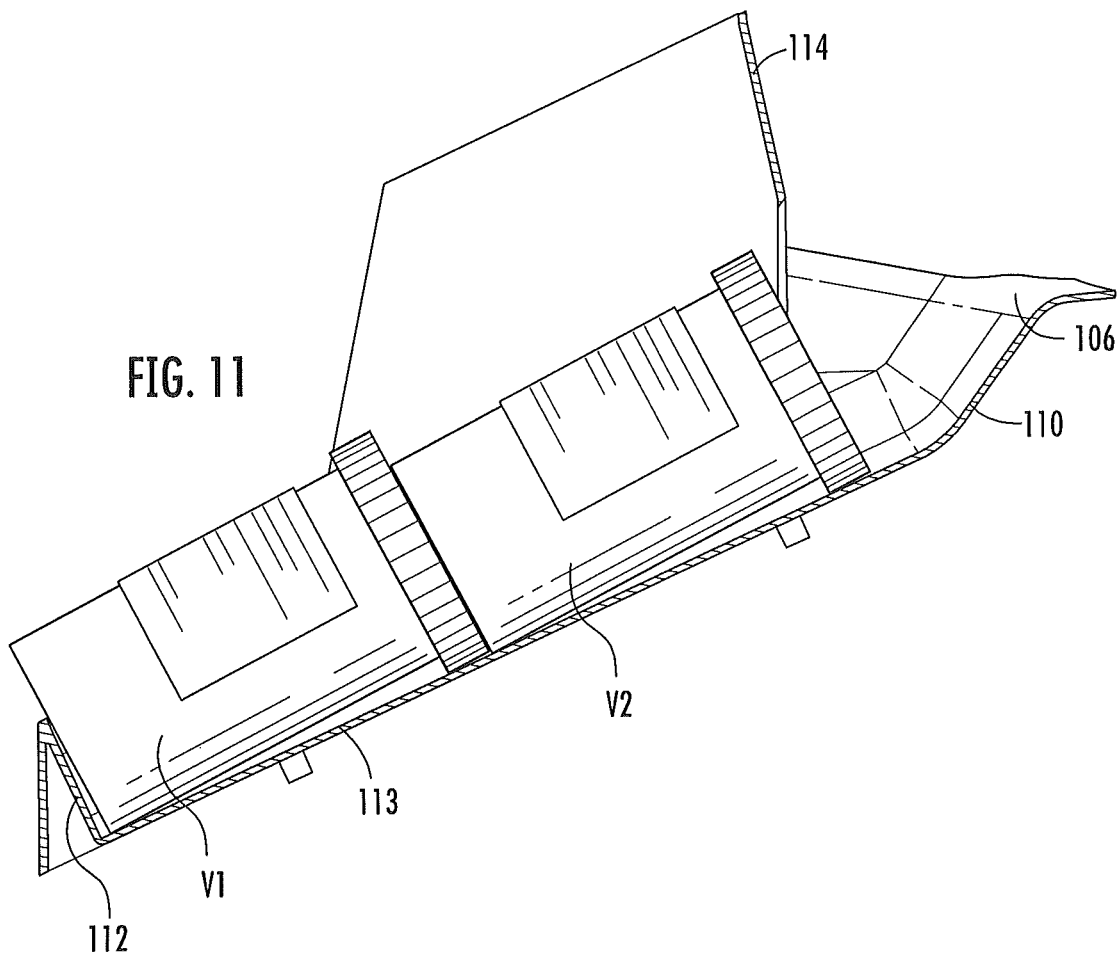
FIG. 11 is a side section view of the chute unit of FIG. 4 illustrating that the trough thereof can hold two vials at once.
Figure 12:
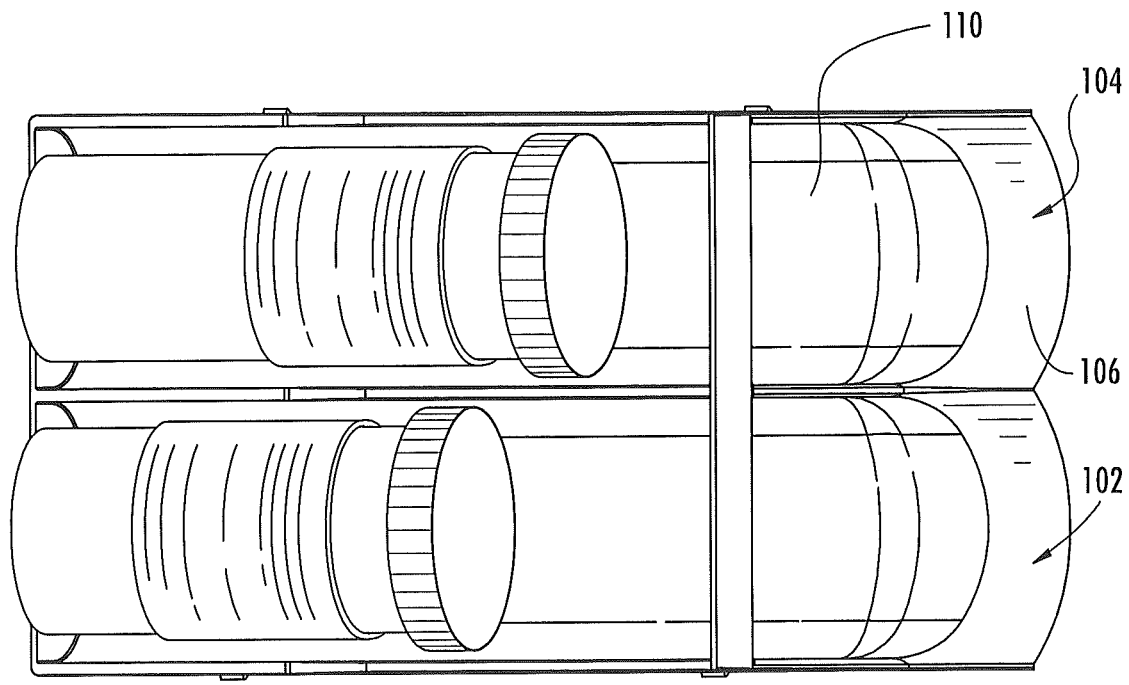
FIG. 12 is a top view of the chute unit of FIG. 4 illustrating that the chutes can hold vials of different sizes.

Once the vial V enters the half-bowl formed by the ramp 110, the side walls 108, 109 and the lip 106, the vial V, oriented "non-capped end down", slides through the inlet 115 (see FIG. 9) and down the trough 112 to the front wall 116 (see FIG. 10), where it rests until pharmacy personnel remove it. In some embodiments, it may be desirable for at least two vials V1, V2 to be stored at once in the trough in a stacked arrangement (see FIG. 11). As such, the trough 112 may have a length of between about 9 and 10 inches, which enables two vials 4 inches in length to be stored and accessible for pharmacy personnel. Also, vials of different sizes can be stored in chutes 102, 104 (see FIG. 12).

Also, the dividers 116, 117 may be configured such that the chute unit 100 satisfies the provisions of UL 61010A-1, 1740 (the requirements of which are hereby incorporated herein by reference), which requires that an object 2.95 in diameter be prevented from entering the inlet 115 (this test is intended to simulate a human hand entering the inlet 115 from outside of the system). In some embodiments, the leading edges 118 of the dividers 116, 117 are positioned between about 5 and 7 inches from the inlet 115 and are between about 2.5 and 2.75 inches apart.

Figure 17:
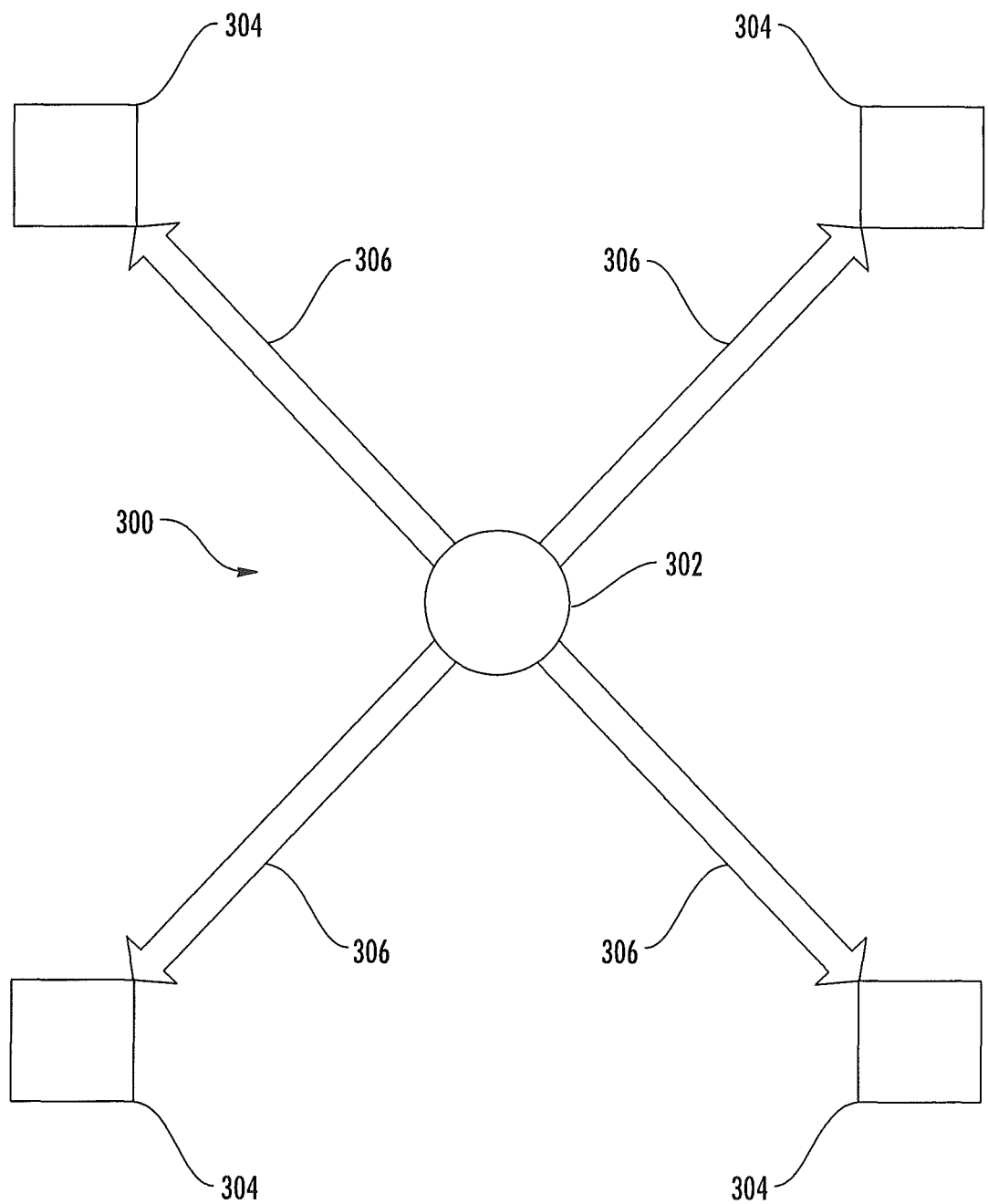
FIG. 17 is a schematic diagram of a "hub-and-spoke" configuration for pharmaceutical distribution that incorporates a pharmaceutical dispensing system similar to that of FIGS. 1-12 serving as the "hub".

In another embodiment, instead of being deposited into the chutes of the offload station 66, the carrier 68 may deliver a filled and capped vial to another location where a tote 61 (FIG. 18), for example, with the capacity to hold many vials simultaneously, is positioned. Such a location may alternatively consist of a box, bin, or other container of appropriate capacity. The tote's contents may be designated for delivery to a pharmacy location different from that where the system 40 is located. Multiple totes 61 may be used with the system 40 simultaneously; in some embodiments each tote 61 may be allocated to a different pharmacy such that the system 40 is filling prescriptions for multiple pharmacies in a "hub and spoke" type of an arrangement, such as that shown in FIG. 17. The hub-and-spoke arrangement 300 includes a pharmacy where a system 40 is located as the "hub" 302 and a number of remote pharmacies 304. Prescription orders from the remote pharmacies 304 are received by the hub 302, filled, and subsequently delivered to the remote pharmacies 304 with the communication and delivery paths between the hub 302 and remote pharmacies 304 considered the "spokes" 306. As prescriptions are processed through the system 40, the controller 42 may, based on the ultimate disposition of each prescription, designate the proper location for offload of each vial from the system 40. Totes 61 may be located in any area of the system 40 that is amenable to such placement. An exemplary location for a tote 61 is the shelf area 65 shown at the end of the system 40 in FIGS. 2 and 3. This may be a desirable location for a tote 61 due to, among other reasons, its proximity to the closure station 64; as closures are applied to filled vials, the carrier 68 would have a shorter distance to travel to drop off the vial. The tote 61 may rest on a shelf; which may be attached to the system 40 or free standing, or the tote 61 may be directly attached to the system 40; the attachment mechanism may be reversible so that the entire tote 61 can be removed for further processing and/or delivery of the contents of the tote 61. Additionally, multiple shelves or attachment locations for tote 61 could be installed to support multiple totes 61 (FIG. 18); this may be desirable to accommodate a large number of prescriptions to be filled for a given pharmacy location and/or to accommodate prescriptions for more than one remote pharmacy location 304, as discussed above.

Figure 18:
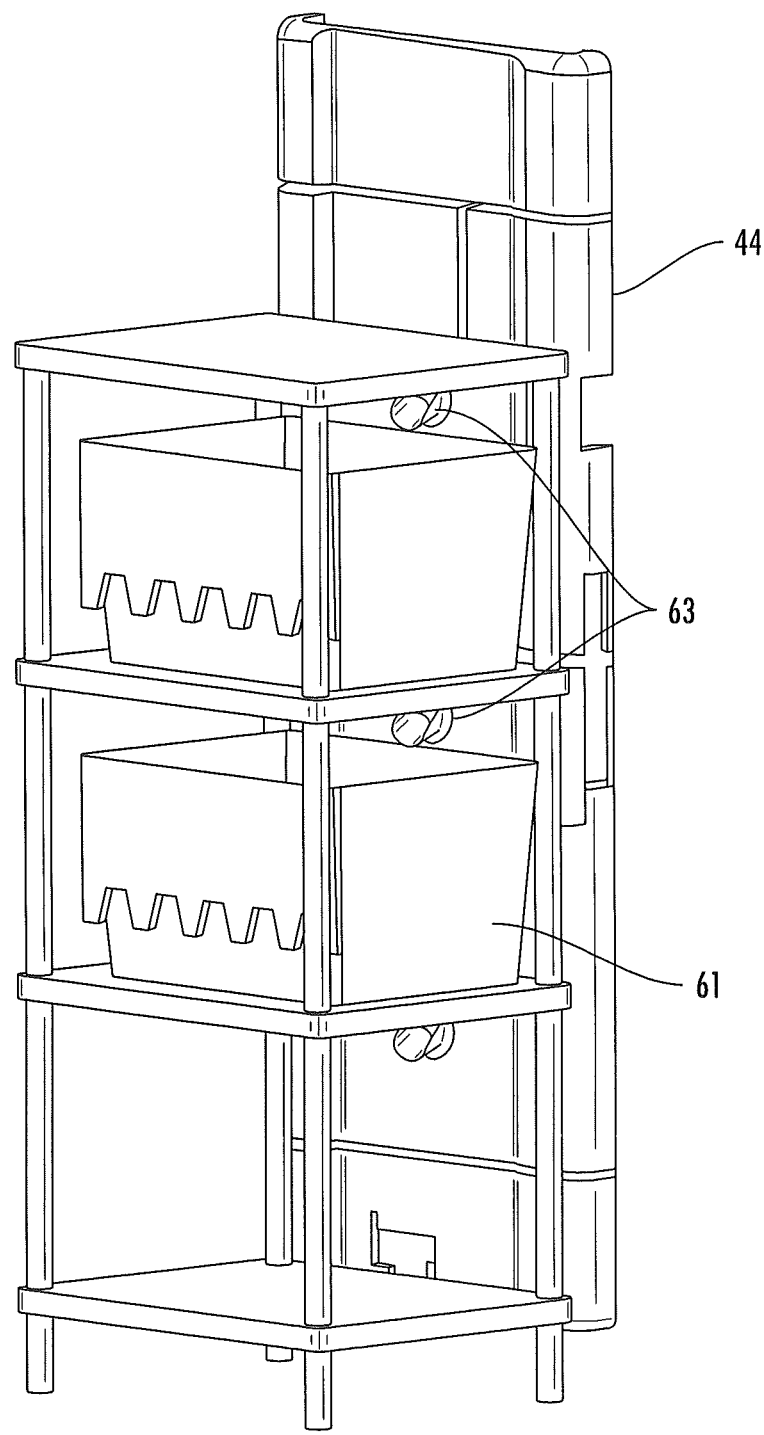
FIG. 18 is a rear perspective view of the system of FIG. 2 showing the addition of chutes and totes for offloading of vials.

Modifications to the system 40 may be made to facilitate this drop-off process such as the installation of a chute 63 (FIG. 18) or ramp to guide the movement of the vials into the tote 61 (FIG. 18). In one embodiment, the chute(s) 63 may be illuminated. In another embodiment, the illumination of the chute(s) 63 may be accomplished using different colored and/or blinking lights, which may be used to indicate the status of the location. An example of one such arrangement is as follows:

| Chute light color/state | Indication | Description/Example |
| --- | --- | --- |
| OFF | System is idle | System off or no tote in place at chute location |
| GREEN | Tote is OK | Tote is in place at that chute location and ready to receive vials |
| YELLOW | Caution, vial in process | The system is currently processing a vial that is destined for that chute/tote |
| FLASHING YELLOW | Attention needed | Exemplary reasons: Tote is full; barcode not readable |
| FLASHING RED | Fault/error/ needs immediate attention | Exemplary reasons: Tote is removed while vial in process for that chute; tote overfilled; chute jammed |

In one embodiment, the system 40 includes one or more sensors to detect the presence or absence of a tote 61 in each location. In another embodiment, the system 40 includes one or more sensors to detect the level of the contents of each tote 61. In still another embodiment, the tote(s) 61 may be designated to hold filled prescriptions that are intended for pick up by patients at a later time (a different day, for example) at the local pharmacy 302 and may be handled differently in the pharmacy's workflow than other prescriptions requiring earlier distribution to patients, which may be dispensed through the offload station 66. The totes 61 and their contents can be designated for any purpose that may make it desirable to segregate a group of filled prescriptions and, thereby, facilitate the workflow of the pharmacy.

Figure 19:
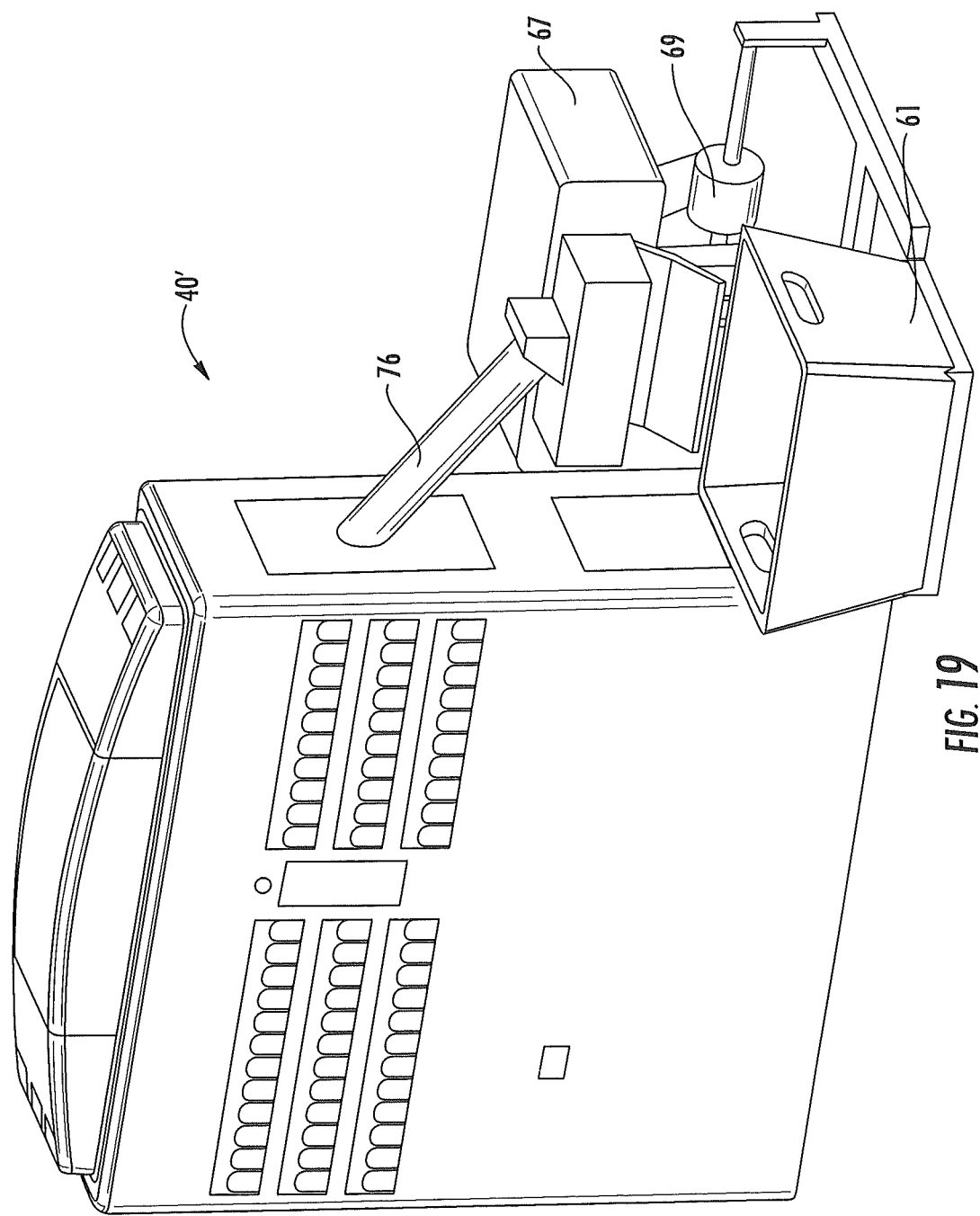
FIG. 19 is a front perspective view of the system of FIG. 2 showing the addition of a chute and an automatic bagging and printing unit, with a tote for offloading of vials.

In another embodiment, exemplified in FIG. 19, the system 40' may include an automatic bagger 67 to bag the prescription vials once the system 40' has completed the filling process. The bagger 67 may be positioned to facilitate receiving the filled prescription vial, such as from a chute 76, directly from the system 40' so that the vial may be placed in a bag prior to placement in the tote 61. One or more filled prescription vials may be placed in a bag; a prescription order for a patient may include more than one vial of medication filled in the system 40' or may include items that must be retrieved from outside the system 40', such as unit of use medications, tubes of ointment, slave, etc., oral contraceptives, prescription medications that must be retrieved from stock bottles, over the counter items, etc. The bag also may have one or more labels 69 with identifying information adhered to it; some nonlimiting examples of identifying information are patient name, patient address, patient phone number, prescription number, drug name, drug dosage, NDC number, drug image, drug description, remote pharmacy name, remote pharmacy identification number, remote pharmacy address, remote pharmacy phone number, etc. The identifying information may be alpha-numeric and/or encoded (e.g., barcode, RFID, etc.). The identifying information may be printed on the labels 69 or directly on the bag by a printer that is associated with or integral to the bagger 67, as shown in FIG. 19. Alternatively, labels 69 may be printed by a separate printing unit and fed into the bagger 67 for application to the bags or may be otherwise applied to the bags. Exemplary bagging and label printing/applying systems may be obtained from Mark-Pack, Inc. of Coopersville, Mich. (www.markpackinc.com). One of skill in the art will recognize that the bagger 67 could be a table-top unit. Additionally, the bagger 67 may receive vials directly from the pharmaceutical dispensing system 40', as shown, or may be manually fed using vials that are filled and separately offloaded from the pharmaceutical dispensing system 40'. Items that may be retrieved from outside the system 40', as discussed above, may be manually fed into the bagger so that they can be included in a grouped order for a customer or, if the design of the system 40' allows, may be dispensed from inside the system 40' as well. Paper documentation also may be included in the bags, such as drug information forms or insurance paperwork, which may be printed at a separate printer or there may be a printer and automatic folding machine included as part of the bagging system and the papers may be automatically added to the bags. Papers may be inserted in the bags before they are closed or may be stapled to or otherwise attached to the outside of the bag. Bags that are released from the bagger 67 may be loaded into a container, such as a tote 61; the container may be used as an interim collection container, may be designated for a particular storage location in the hub pharmacy 302, or may hold bags which are designated for an off-site location, such as a remote pharmacy 304.

Figure 14:
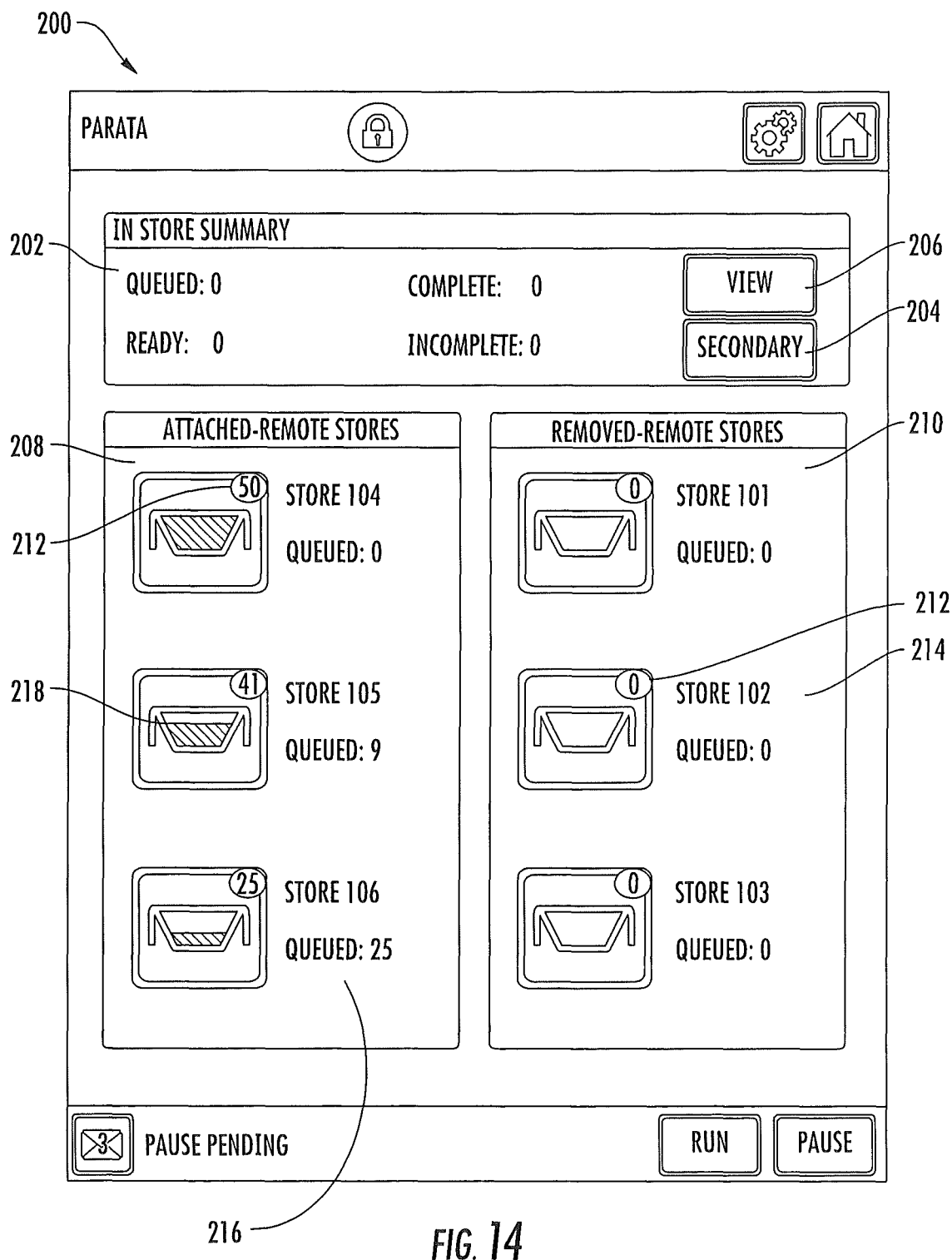
FIG. 14 is a Home screen of the system graphical user interface.

In a particular embodiment, the system graphical user interface (GUI) includes a portion specific to the filling of totes 61 to facilitate user interaction with and monitoring of the system 40 during tote 61 filling. Details of an exemplary GUI are set forth in U.S. Patent Application Publication No. 2009/0287350, the disclosure of which is hereby incorporated by reference herein in its entirety. Referring now to FIG. 14, in some embodiments the Home screen 200 the GUI may include an In Store Summary portion 202, where a high level status of prescriptions entered into the system 40 for fulfillment is shown. The Home screen 200 may include a Priority button 204 which allows the user to select whether the prescriptions for the local pharmacy 302 or the prescriptions entered for one or more remote pharmacies 304 are given priority in the filling process. A View button 206 allows the user to switch between the view of the GUI for tote 61 filling and a view of the GUI for the local system 40, which includes the offload station 66, if desired. The GUI may include an Attached Totes display 208 showing information pertaining to those totes 61 currently associated with the system 40 for filling. The GUI may include a Removed Totes display 210, showing information pertaining to totes 61 currently not associated with the system 40. Each of the Attached Totes 208 and Removed Totes 210 displays may communicate information about the status of the totes 61 such as the number of prescriptions in the tote 212, the designation of the store assigned to the tote 214, and the number of prescriptions directed to that tote 216. In one embodiment, the graphic for each tote 61 includes a dynamic fill line 218 that moves higher on the representation of the tote 61 as vials are added to that tote 61 and serves as a graphic indicator of the fill status of that tote 61. The dynamic fill level for each tote 61 may also include a color indicator. For example, the fill line for: a tote 61 that is full may be colored in red; a tote 61 that is near full (over a threshold level but not full) may be colored in yellow; and a tote 61 that under a threshold level may be colored in green.

Figure 15:
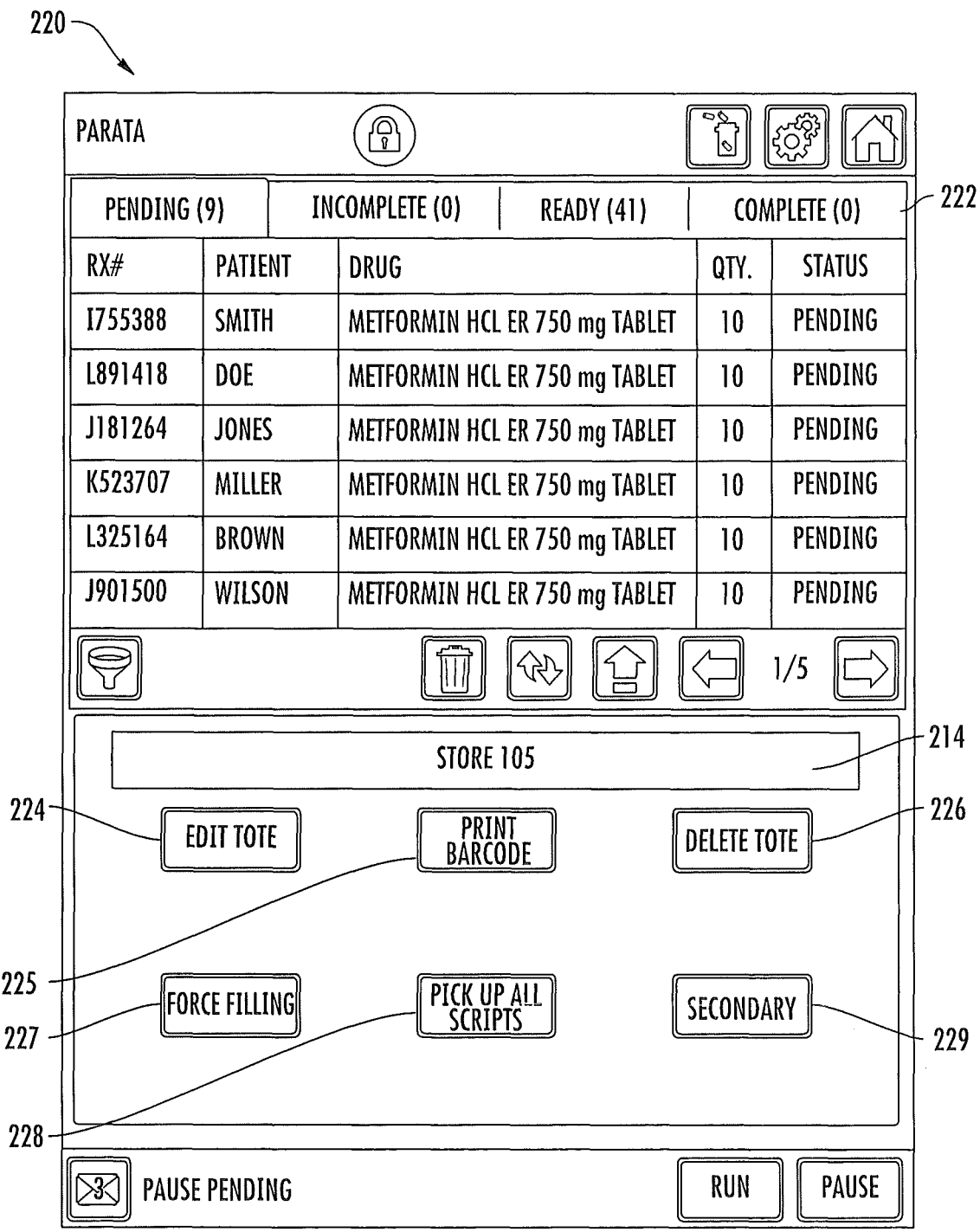
FIG. 15 is a Tote View screen of the tote offload portion of the system graphical user interface.

Turning now to FIG. 15, the GUI may include a Tote View screen 220 that displays information specific to that tote 61 and, therefore, a particular remote pharmacy 304. The Tote View screen 220 displays the designation of the store assigned to the tote 214. Such designation can be indicated in any of various ways such as by number, name, color, logo or any other unique identifier, which also can be present on the tote 61, in the form of alphanumeric text, RFID label, barcode, logo, graphics, etc. The Tote View 220 screen also comprises status tabs 222 (Pending, Incomplete, Ready and Complete, for example) which include an indication of the number of prescriptions identified by that status. The user may select a status tab to view a list of prescriptions associated with this status and the details of each prescription.

The Tote View screen 220 may also include various buttons for different functions or preferences related to the selected tote 61. Some of these functions may include editing the settings associated with the tote (button 224), such as the store name, printing a barcode for the tote (button 225), or deleting a tote from the application (button 226). It may be desirable to fill the prescriptions for a given tote 61 regardless of the status of the tote 61 (i.e., even if the sensors indicate that the tote 61 is full or absent); the Force Filling button 227 can be selected to perform this function. When all of the prescriptions for a given tote 61 have been filled (i.e., are in the "Ready" queue), the user can select the Pick Up All Scripts button 228 which will move all of the prescriptions for that tote 61 into Complete status in the system 40 (under local filling conditions, the bar code for each prescription would have to be scanned individually to move that prescription to Complete status in the system 40). The Tote View screen 220 may also include a Priority button 229; in this case the selection of priority will assign preference in the filling process to the prescriptions for the particular tote 61.

Figure 16:
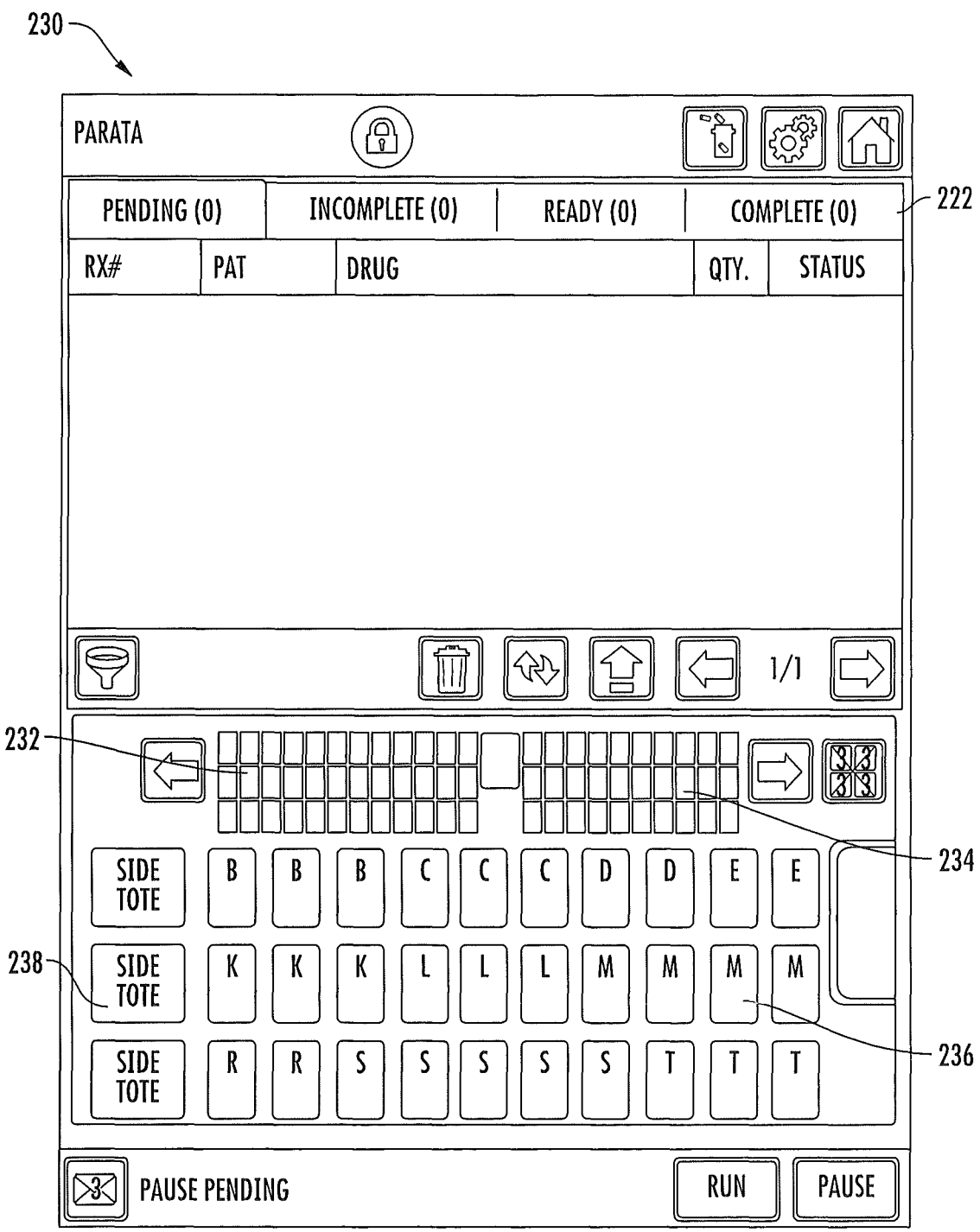
FIG. 16 is an In-Store screen of the system graphical user interface.

All of the locations for offload of filled prescription vials may be visualized in the In-Store GUI screen 230, as exemplified in FIG. 16. The offload station 66 is represented graphically at 232 and 234. The locations labeled "B", "C", "D", "E", . . . , "T" 236 represent the individual locations of the graphical representation 232 of the offload station 66. The locations of the other portion of the offload station 66 can be displayed by scrolling through the other locations of section 232 and 234. The totes 61 are represented by the Side Tote locations 238.

In some embodiments, it may be desirable to allow the system 40 to operate unattended. In this way the system 40 still may be productive when the pharmacy is closed or otherwise slow, to maximize the volume of prescriptions filled by the system 40 and/or for strategic use of system 40 time. For example, when the pharmacy is closed or during slow periods when the pharmacy is open, the system 40 can fill prescriptions for later retrieval by the pharmacy's own customers (i.e., refills, non-urgent prescriptions that customer indicates will be picked up at later time). In another embodiment, the system 40 may operate to fill prescriptions for other pharmacy locations during these slower/overnight/closed operational periods; these prescriptions would then be delivered to the appropriate location once the orders are complete (hub and spoke arrangement).

In another embodiment, the imaging feature (discussed above) may be included in the system 40 during unattended operation. With the images available for all prescriptions filled during unattended operation, the images for prescriptions contained in each tote 61 can be viewed by the pharmacist prior to releasing the tote 61 for delivery to the remote pharmacy 304. In some embodiments, the images for all prescriptions contained in a tote 61 may be viewed by a remote pharmacist so that the remote pharmacist can provide verification that each prescription has been filled correctly prior to release of the tote 61 and delivery to the appropriate pharmacy. In some embodiments, the remote pharmacist may review the images for prescriptions filled by the system 40 to be delivered to customers at the hub pharmacy 302; once the pharmacist has verified that the prescription has been filled correctly, it may be released for delivery to the customer. For clarity, a "remote pharmacist" may be located anywhere other than with the system 40 at the hub pharmacy 302 and may or may not be located at one of the remote pharmacies 304. One of skill in the art will recognize that the functions described herein as being performed by a remote pharmacist may alternatively be performed by a pharmacist located proximate to the system 40 (i.e., at the hub pharmacy 302). The system 40 may be configured to provide messages via text message, instant message, email, voice message, or any other form of message; these messages would be delivered to pre-designated phone number(s) or email address(es) upon certain situations that may arise, particularly during unattended operation of the system 40. Such messages may include indications of the following:

- System error (i.e., mechanical malfunction, system inoperable, insufficient vial/label/cap/drug/bag inventory to complete a prescription fill, etc.)
- Power failure
- Full tote(s)
- Service needed
- Low inventory in system (i.e., drugs, vials, caps, labels, bags)
- Problems with prescription filling process (i.e., capping error, labeling error, bagging error, etc.)
- Prescription orders complete for delivery to specific remote location Messages may include specific instructions related to the message, as may be programmed into the system 40. For example, a message indicating that the prescription orders are complete for a specific remote location 304 may include instructions to schedule the delivery of the tote(s) 61 to the appropriate remote location 304; this message may be sent directly to the delivery organization as notification that the prescriptions are ready for pick-up and delivery to the remote location 304. A message indicating that one or more totes 61 is/are full may include instructions to remove the tote(s) 61 and replace it/them with an empty tote 61, possibly of a specific type (i.e., a specific size and/or belonging to specific remote location). A message indicating low inventory in the system 40 may include information regarding which locations of the tablet dispensing station 62 need to be refilled and with which drug, or that the vials or caps (of a specific size) need to be refilled, etc. Messages indicating that the system 40 is inoperable or that service is needed may be sent directly to a repair person with a request for service on the system 40 and may contain specific information on the type of service required.

Figure 21:
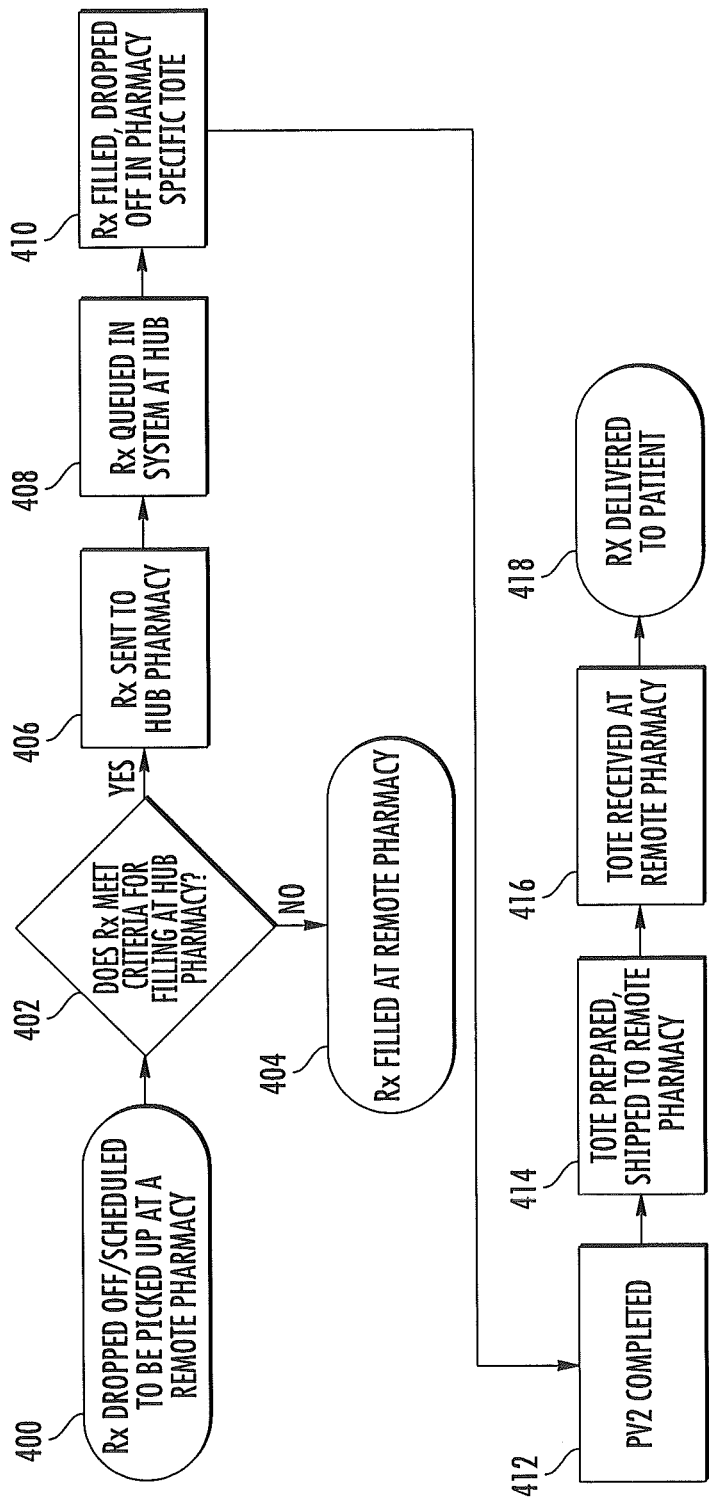
FIG. 21 is a flow chart illustrating exemplary operation of the system for filling of prescriptions in a "hub and spoke" arrangement.

An exemplary process for filling prescriptions in a hub and spoke pharmacy arrangement, as discussed above, is illustrated in FIG. 21. As shown in FIG. 21, a patient's prescription is entered into the pharmacy management system of a remote pharmacy 304 and scheduled to be picked up at the same location (Block 400). For a prescription to be entered in the system, the patient may drop off a paper prescription at the remote pharmacy 304, may request a refill (over the phone or in person), or may place an order electronically. Additionally, the prescription may be entered at the remote pharmacy 304 by a phone call or electronic order from the ordering physician or by transfer from another pharmacy. Once the details of the prescription order are entered, the system queries whether the prescription order meets criteria for filling of the prescription at the hub pharmacy 302 (Block 402). The criteria that are evaluated may include considerations such as pharmaceutical inventory at the hub pharmacy 302, urgency of the prescription, scheduled pick-up date/time, etc. If the criteria for fulfillment at the hub pharmacy 302 are not met, the prescription is filled at the remote pharmacy 304 (Block 404). If the criteria for fulfillment at the hub pharmacy 302 are met, the prescription information is sent to the hub pharmacy 302 (Block 406). The prescription may be received by a component of the hub pharmacy's pharmacy management system, a separate server, or the system 40 itself. The prescription enters the queue of the system 40 (Block 408), its location in the queue determined by criteria at the hub pharmacy 302; these criteria may include filling priority, the availability of the appropriate drop-off location (tote 61), system 40 inventory, delivery schedule for the tote 61, etc. The prescription is filled (Box 410) by the steps illustrated in FIG. 1. The offloading of the filled, secured container (Box 38 of FIG. 1) is accomplished by delivery of the prescription to the appropriate tote 61 for the remote pharmacy 304. The system 40 also may include a camera 72 to capture an image of the vial contents or a scale to obtain the weight of the vial and its contents, respectively, as discussed above. The next step in the process is verification by a pharmacist that the prescription has been filled as ordered (PV2) (Block 412). The PV2 step may be completed by a pharmacist at the hub pharmacy 302; this process can be facilitated by the pharmacist's review of the images of each prescription so that the pharmacist does not have to open each vial (this approach is a particular advantage if the prescriptions are bagged prior to release into the tote 61). Alternatively, automated image analysis of the captured images may be performed for the PV2 step, which also is advantageous when the vials are bagged prior to release into the tote 61. PV2 may be performed by a pharmacist at a remote location, whether it be that of the remote pharmacy 304 from which the prescription was received or another pharmacy different from the hub pharmacy 302; the images of the filled prescriptions and the prescription information may be sent electronically to another location where a pharmacist can view the available information and perform the verification of the filled prescription. An indication of the prescription's verification status, such as verified or rejected, may be indicated on the label or bag. When all prescriptions for a given remote pharmacy location 304 have been filled, the tote 61 is prepared and sent to the remote pharmacy 304 (Block 414). Preparation of the tote 61 may include the preparation of a manifest or other documentation, which may include order identification numbers, item numbers, quantity, barcodes, etc., in addition to delivery information or other information; information about the tote 61, its destination, contents, etc. may be in alphanumeric text, or may take the form of a unique code, which may be a bar code, RFID label, or other code. The manifest or other documentation may be printed by choosing a button on the GUI (not shown). Preparation of the tote 61 also may include bagging of the filled prescriptions, if they have not already been bagged prior to release into the tote 61, as discussed above, or packaging into a secondary type of package. Alternatively, the prescriptions may be placed in bags at the remote pharmacy 304, prior to distribution to the patient or patient representative picking up the prescription from the remote pharmacy 304. When the tote 61 is received by the remote pharmacy 304 (Block 416), the prescriptions are distributed to the patient or their representative when they arrive for pick-up (Block 418). The filled prescriptions may be temporarily stored in a will call device or will call area of the remote pharmacy 304 to await pick up.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. For example, many types of error messages, specific message content, instructions and message delivery destinations are possible and evident to one of skill in the art with the teachings of this invention. As another example, the types of GUI screens, information displayed and functional buttons may be tailored to facilitate the workflow of the pharmacy and the particular assignment of totes (i.e., whether for delivery to a remote pharmacy, for in-store patient pick-up, or other destination or categorization). Additionally, a variety of different light locations as well as different color and pattern combinations can be implemented to provide information regarding the status of the system and specific totes or chutes. While prescriptions may be entered at a remote pharmacy and scheduled to be picked up at the same pharmacy, the prescription can be scheduled to be picked up at any pharmacy, without changing the teachings and advantages of this invention. Prescriptions may be verified (PV2) manually by a pharmacist at either the hub pharmacy or when they are received at the remote pharmacy, prior to delivery to the patient. Accordingly, all such modifications are intended to be included within the scope of this invention as defined in the claims. The invention is defined by the following claims, with equivalents of the claims to be included therein.

That which is claimed is:

1. A pharmaceutical dispensing system, comprising:
a frame;
a plurality of cells configured to house pharmaceutical pills;
a processor;
memory coupled to the processor;
at least one offload location;
a tote to receive vials at each offload location, the tote assigned for distribution to a remote pharmacy location;
at least one detection sensor to detect the presence or absence of the tote;
at least one fill sensor to detect a fill level in the tote of the vials; and
a GUI, wherein the GUI includes a portion specific to filling of the tote;
wherein the processor is configured to provide an alert when the tote is full; and
wherein the processor is configured to create a message when the tote is full instruct a recipient to replace the full tote with another tote.

2. The pharmaceutical dispensing system of claim 1, wherein the GUI communicates information about a status of the tote.

3. The pharmaceutical dispensing system of claim 2, wherein the status is at least one of: the association of the tote with the system, a number of vials in the tote, a designation of the pharmacy location assigned to the tote; a number of vials directed to the tote, and a fill level of the tote.

4. The pharmaceutical dispensing system of claim 3, wherein the status is the fill level of the tote, and wherein the fill level of the tote is indicated by at least one of a dynamic fill line or a color.

5. The pharmaceutical dispensing system of claim 1, further comprising a camera for capturing images of filled vials.

6. The pharmaceutical dispensing system of claim 1, further comprising a bagger for automatically inserting filled vials into bags.

7. The pharmaceutical dispensing system of claim 5, further comprising a computer program residing in the memory that is executable by the processor for automatically analyzing the images captured by the camera.

8. The pharmaceutical dispensing system of claim 6, wherein the bagger further comprises a printer for printing identifying information on a label or on a bag.

9. The pharmaceutical dispensing system of claim 6, wherein documentation is added to one or more of the bags.

10. The pharmaceutical dispensing system of claim 1, wherein in the portion of the GUI specific to filling of the tote allows a user to create a manifest for the tote.

* * * * *